United States Patent
Andersen et al.

(10) Patent No.: US 7,771,960 B2
(45) Date of Patent: Aug. 10, 2010

(54) FELINE PANCREATIC LIPASE

(75) Inventors: Philip Andersen, Poland, ME (US);
Melissa Jane Beall, Cape Elixabeth, ME (US); Jesse Buch, Kennebunk, ME (US);
Ku-chuan Hsiao, Easton, PA (US);
Stacey Pazar Huth, Yarmouth, ME (US); Eugene Regis, Freeport, ME (US);
Barbara O'Brien, Gorham, ME (US);
Marilyn Strong-Townsend, Yarmouth, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 6 days.

(21) Appl. No.: 12/252,120

(22) Filed: Oct. 15, 2008

(65) Prior Publication Data
US 2009/0098576 A1    Apr. 16, 2009

Related U.S. Application Data

(60) Provisional application No. 60/980,029, filed on Oct. 15, 2007.

(51) Int. Cl.
*G01N 33/573* (2006.01)
*G01N 33/53* (2006.01)
*C07K 16/18* (2006.01)

(52) U.S. Cl. .................. 435/7.4; 435/7.1; 435/7.2; 435/7.9; 435/7.92; 435/7.93; 435/7.94; 435/7.95; 435/338; 530/388.26

(58) Field of Classification Search ............ None
See application file for complete search history.

(56) References Cited

U.S. PATENT DOCUMENTS

| | | |
|---|---|---|
| 3,817,837 A | 6/1974 | Rubenstein et al. |
| 3,996,345 A | 12/1976 | Ullman et al. |
| 4,486,530 A | 12/1984 | David et al. |
| 4,555,483 A | 11/1985 | LiMuti et al. |
| 4,845,028 A | 7/1989 | Imamura et al. |
| 4,948,723 A | 8/1990 | Hermon-Taylor et al. |
| 5,093,256 A | 3/1992 | Shen et al. |
| 5,173,417 A | 12/1992 | Takeda et al. |
| 5,185,243 A | 2/1993 | Ullman et al. |
| 5,219,753 A | 6/1993 | Berka et al. |
| 5,232,846 A | 8/1993 | Takeda et al. |
| 5,244,798 A | 9/1993 | Takeda et al. |
| 5,248,598 A | 9/1993 | Kwan et al. |
| 5,328,832 A | 7/1994 | Miki et al. |
| 5,378,609 A | 1/1995 | Kwan et al. |
| 5,449,607 A | 9/1995 | Wilton |
| 5,726,010 A | 3/1998 | Clark |
| 5,750,333 A | 5/1998 | Clark et al. |
| 5,849,296 A | 12/1998 | Navia et al. |
| 5,976,529 A | 11/1999 | Navia et al. |
| 6,004,768 A | 12/1999 | Navia et al. |
| 6,074,863 A | 6/2000 | Svendsen et al. |
| 6,297,014 B1 | 10/2001 | Taylor et al. |
| 6,322,993 B1 | 11/2001 | Schelong et al. |
| 6,337,187 B1 | 1/2002 | Kapeller-Libermann |
| 6,489,309 B1 | 12/2002 | Singh et al. |
| 6,558,936 B1 | 5/2003 | Khodadoust et al. |
| 6,797,502 B2 | 9/2004 | Kapeller-Libermann |
| 6,855,506 B2 | 2/2005 | Steiner et al. |
| 6,864,064 B2 | 3/2005 | Kapeller-Libermann |
| 2002/0052034 A1 | 5/2002 | Guegler et al. |
| 2003/0207333 A1 | 11/2003 | Steiner et al. |
| 2005/0233368 A1 | 10/2005 | Beall et al. |

OTHER PUBLICATIONS

Abstract: Steiner, et al., Canine Pancreatic Lipase Immunoreactivity Test (cPLI) (Texas A & M University); www.cvm.tamu.edu; (2000).

Abstract: Pancreatic Lipase Immunoreactivity (cPLI) Test for diagnosis of pancreatitis in dogs only; GI Lab, College of Veterinary medicine, Texas A & M University; (1999).

Abstract: Steiner, et al., Development and Validation of a Radioimmunoassay for the Measurement of Canine Pancreatic Lipase Immunoreactivity (cPLI) in Serum; ACVIM Poster Abstract 201 (2000).

Confluolip™ Pancreatic Lipase Test Package Insert, www.reasearchd.com (2002).

DeCaro, Josiane, et al., *Pancreatic lipase-related protein 1 (PLRP1) is present in the pancreatic juice of several species*, Biochemie et Biophysica Acta, 1387:331-341 (1998).

Tan, S.W., et al., *Production and Characterization of Murine Monoclonal Antibodies to Blastocystis hominis*, International Journal for Parasitology, 26(4):375-381 (1996).

(Continued)

*Primary Examiner*—Robert B Mondesi
*Assistant Examiner*—Padma V Baskar
(74) *Attorney, Agent, or Firm*—McDonnell Boehnen Hulbert & Berghoff LLP

(57) ABSTRACT

Isolated nucleic acid molecules having a nucleotide sequence encoding feline pancreatic lipase polypeptides, splice variants, allelic variants, and fragments thereof. Isolated feline pancreatic lipase polypeptides, splice variants, allelic variants, and fragments thereof. Host cells comprising a vector containing the polynucleotide sequences and methods for expressing the polypeptides. The generation of monoclonal antibodies that specifically binds to the feline pancreatic lipase polypeptides, and cell lines secreting the monoclonal antibodies. Methods for determining the presence or amount of feline pancreatic lipase in a biological sample. The methods include using standards or calibrators of recombinant feline pancreatic lipase to quantify the lipase in a sample. Devices and kits for performing methods for detecting feline pancreatic lipase in biological samples.

22 Claims, 9 Drawing Sheets

OTHER PUBLICATIONS

Aoubala, Mustapha, et al., *Human Pancreatic Lipase*, The Journal of Biological Chemistry, 270(8):3932-3937 (1995).

Visai, Livia, et al., *Identification and characterization of a new ligand-binding site in FnbB, a fibronection-binding adhesion from Streptococcus dysgalactiae*, Biochimica et Biophysica Acta 1646:173-183 (2003).

Lowe, et al., *Cloning and Characterization of Human Pancreatic Lipase cDNA*, Journal of Biological Chemistry, 264(33):20042-20048 (1989).

Mickel, F. Susan, et al., *Structure of the Canine Pancreatic Lipase Gene*, The Journal of Biological Chemistry, 264:12895-12901 (1989).

Quigley, et al., *Hyperlipasemia in 6 Dogs with Pancreatic or Hepatic Neoplasia: Evidence for Tumor Lipase Production*, Veterinary Clinical Pathology, 30:114-120 (2001).

Peterson, et al., A sequence analysis of lipases, esterases and related proteins, Lipases—their structure, biochemistry and application, Woolley, P. and Peterson, S., eds., Cambridge University Press, pp. 23-48 (1994).

Lin et al., *Substrate Specificities of Lipases from Corn and Other Seeds*, Archives of Biochemistry and Biophysics, 244:346-356 (1986).

Jaeger, et al., *Bacterial lipases*, FEMS Microbiology Reviews, 15:29-63 (1994).

Mukherjee, K.D., et al., *Lipases from plants*, Lipase—their structure, biochemistry and application, Woolley, P. and Peterson, S., eds., Cambridge University Press, pp. 49-75 (1994).

Lawson, David, et al., *The three-dimensional structures of two lipases from filamentous fungi*, Lipase—their structure, biochemistry and application, 77-94 (1994).

Svendsen, Allan, *Sequence comparisons within the lipase family*, Lipase—their structure, biochemistry and application, Woolley, P. and Peterson, S., eds., Cambridge University Press, pp. 1-21 (1994).

Antonian, Edna, *Recent Advances in the Purification, Characterization and Structure Determination of Lipases*, Lipids, 23:1101-1106 (1988).

Carrière, Frédéric, *Molecular evolution of the pancreatic lipase and two related enzymes towards different substrate selectivities*, Journal of Molecular Catalysis B: Enzymatic, 3:55-64 (1997).

Carrière, Frédéric, *Structural basis for the substrate selectivity of pancreatic lipases and some related proteins*, Biochimica et Biophysica Acta, 1376:417-432 (1998).

Hirata, Ken-ichi, et al., *Cloning of a Unique Lipase from Endothelial Cells Extends the Lipase Gene Family*, The Journal of Biological Chemistry, 274:14170-14175 (1999).

Anderson, Richard, et al., *Cloning and Expression of cDNA Encoding Human Lysosomal Acid Lipase/Cholesteryl Ester Hydrolase*, The Journal of Biological Chemistry, 266:22479-22484 (1991).

Carriere, Frederic, et al., *Gastric lipases: cellular, biochemical and kinetic aspects*, Lipase—their structure, biochemistry and application, Woolley, P. and Peterson, S., eds., Cambridge University Press, pp. 181-205 (1994).

Moreau, Hervé, et al., *Screening of preduodenal lipases in several mammals*, Biochimica et Biophysica Acta, 959:247-252 (1988).

Carriere, Frederic, et al., *Secretion and Contribution of Lipolysis of Gastric and Pancreatic Lipases During a Test Meal in Humans*, Gastroenterology, 105:876-888 (1993).

Carriere, Frederic, et al., *Gastric and Pancreatic Lipase Levels during a Test Meal in Dogs*, Scand J. Gastroenterol, 28:443-454 (1993).

Carriere, Frederic, et al., *Purification and biochemical characterization of dog gastric lipase*, Eur. J. Biochem, 202:75-83 (1991).

Steiner, Jorg, et al., *Cellular immunolocalization of gastric and pancreatic lipase in various tissues obtained from dogs*, American Journal of Veterinary Research, 63:722-727 (2002).

Rathelot, Joelle, et al., *Horse pancreatic lipase. Interaction with colipase from various species*, Biochimie, 63: 227-234 (1981).

Bosc-Bierne, Isabelle, et al., *Studies on Chicken Pancreatic Lipase and Colipase*, Biochimica et Biophysica Acta, 794:65-71 (1984).

Mejdob, Hafedh, et al., *Dromedary pancreatic lipase: Purification and structural properties*, Biochimica et Biophysica Acta, 1213: 119-126 (1994).

Steiner, Jorg, et al., *Purification of classical pancreatic lipase from dog pancreas*, Biochimie 84: 1243-1251 (2002).

Steiner, Jorg, et al., *Development and analytic validation of an enzyme-linked immunosorbent assay for the measurement of canine pancreatic lipase immunoreactivity in serum*, The Canadian Journal of Veterinary Research, 67:175-182 (2003).

Steiner, Jorg, et al., *Development and validation of a radioimmunoassay for the measurement of canine pancreatic lipase immunoreactivity in serum of dogs*, American Journal of Veterinary Research, 64:1237-1241 (2003).

Kemppainen, Esko, et al., *Advances in the laboratory diagnostics of acute pancreatitis*, Ann Med, 30:169-175 (1998).

Leger, Claude, et al., *Binding Between Immobilized Anti-Colipase Purified Antibodies and Colipase*, Biochimica et Biophysica Acta, 713:208-221 (1982).

Loor, Rueyming, et al., *Purification and Characterizatoin of a Human Pancreas-Specific Antigen*, Biochimica et Biophysica Acta, 668:222-234 (1981).

Dezan, Christine, et al., *Monoclomal Antibodies to Human Pancreatic Procolipase: Production and Characterization by Competitive Binding Studies*, Hybridoma 13:509-517, 1994.

Carrere, Jaqueline, et al., *Assay of human pancreatic lipase in biological fluids using a non-competitive enzyme immunoassay*. Clinica Chimica Acta, 161:209-219 (1986).

Ohta, Tetsuo, et al., *Presence of Pancreatic α-Amylase, Trypsinogen, and Lipase Immunoreactivity in Normal Human Pancreatic Ducts*, Pancreas, 9:382-386 (1994).

Uhl, W., et al., *Determination of Pancreatic Lipase by Imunoactivation Technology*, International Journal of Pancreatology, 3:253-261 (1992).

Gieseg, S.P., et al., *The Purification of Ovine Pancreaticc Lipase that is Free of Colipase Using an Improved Delipidation Method*, Pancreas, 7:45-51 (1992).

Steiner, J.M. et al., D.A. 2001a, *Serum canine pancreatic lipase immunoreactivity (cPLI) concentrations in dogs with spontaneous pancreatitis*, J. Vet. Int. Med. 15, 274.

Steiner, J.M., et al., D.A. 2000b, *Serum canine pancreatic lipase immunoreactivity (cPLI) concentrations in dogs with exocrine pancreatic insufficiency*, J. Vet. Int. Med. 15, 274.

Steiner, J.M., et al. D.A. 2000c, *Development validation of an enzyme-linked immunosorbent assay (ELISA) for the measurement of canine pancreatic lipase immunoreactivity (cPLI) in serum*, J. Vet. Int. Med. 15, 311.

Campbell, A., Monoclonal Antibody Technology, 1985, pp. 1-32.

Forman, et al., *Evaluation of Serum feline Pancreatic Lipase Immunoreactivity and Helical Cmputed Tomography Versus Conventional Testing for the Diagnosis of Feline Pancreatitis*, J. Vet Intern Med., 18:807-815 (2004).

Thirstrup, et al., *One-step purification and characterization of human pancreatic lipase expressed in insect cells*, Federation of European Biochemical Societies, 327:79-84 (1993).

Figure 1
Primer Design

Primers for 3' RACE
RACE 5   5' gatcctgccctgagcccchraggaygtsra 3' (SEQ ID. NO:4)
UPM      5'CTAATACGACTCACTATAGGGCAAGCAGTGGTATCAACGCAGAGT 3' (SEQ ID. NO:5)
         5'CTAATACGACTCACTATAGGGC 3' (SEQ ID. NO:6)

Primers for 5' RACE
UPM      5'CTAATACGACTCACTATAGGGCAAGCAGTGGTATCAACGCAGAGT 3' (SEQ ID. NO:5)
         5'CTAATACGACTCACTATAGGGC 3' (SEQ ID. NO:6)
Kc616    5'CACCCTTCTGCCCCCACAATCCG 3' (SEQ ID. NO:7)

Primers for full length fPL PCR product
Kc626    5'AAGAATTCAGCCACCATGCTGCTAATCTGGACACTA 3' (SEQ ID. NO:8)
Kc630    5'TCGCGGCCGCTCAACACGGAGTAAGAGTGAGCAGA 3' (SEQ ID. NO:9)

Primers for subcloning into pBAC1
fpl-4_xho1Stop 5' GCTCGAGCTACTATGCACACGGGGTAAGAGTG 3' (SEQ ID. NO:10)
fpl-3_HindIII  5' CAAGCTTACCATGGTGCTAATCTGGACACTATC 3' (SEQ ID. NO:11)

Figure 3 fPL cDNA Sequence

```
atg cta atc tgg aca cta ttt tcg ctg ctg gga gca gta gga aaa gaa atc tgc     60
ttc cca aga ctt ggc tgc ttt cct gat gcc cca aat gat cat aca gtt gta ccc    120
ctc aaa ata ttg aat aga cca aaa att ttc aac acc gcg ctg tca tcg ttt act    180
gag aac acc cga gat tcc aaa aga ata act tgc aag atg aag aac tct atc atc    240
ttt aac tgg aca aga agt gtt ttg ttt aca tat cat aca act agt ata gca gtg    300
aac tgg ctg tgg gca gaa agt ggt aaa acc ttg ggt gaa ctt ttt gga aac ggg    360
gtg gac gtg ggt gca ggg tgg ggt ttg ggc tca cag ctc acc gcc tca gta cag    420
tcc aac aat gtc cac atc cac gtt atc ggg cac agt ctg ggg gcc cac gct ttg    480
agg ctg aca atc aat ccc aaa gac ggg cga tta aca cca ttt gat gct gct atc    540
ggc aca gac gct gct ttc gcc ata aat ctc ccc gac atg ggg agc cag ctg atg    600
aca gat gca tat gat ggc ata ata aca ctg ccc gaa gac tat gtc tta ttt cag    660
cta gtt ttg gtg cat aag ggt ctc aac ttt ggc ttt cgt aca cca tct ttg cct    720
cct gtt tac ttt gct ttt gct gat cct gct aga cgt aac ttt cct cca aag aac    780
tgc cca gat gtt ttc aac tat cat aac cac aga cat tcc tgg agg tgg aag cag    840
ata ggc tat tat cta aac acg agt tat acc aga gat gtt gat aat cat cat ctt    900
gtc acg cag ctg tct aaa ggg gca gtt ttc act aca acc ttc cca gga gtt gga    960
ggg aat ctt gaa ttt caa ata cca gat gtt aag ggg ttt gtc tgc tcg aaa cag   1020
aac gaa gac ttg ttt gat aac atg tta ttg cca aga atc ccg gat gat att act    ... // placeholder row
aac tgg ata aaa gat atc cat aac agc aca tgg ttc aga ctc ata gga cca aga
act ctt acc ccg aaa tgt tgt tag (SEQ ID NO. 2)                              1398
```

FIG. 3

Figure 4 fPLP Amino Acid Sequence

```
MLLIWTLSLL LGAVVGKEIC FPRLGCFSDD APWAGIAQRP LKILPWPPKD VNTRFLLYTN   60
ENPNNFEEII ADESTIMSSN FNTDRKTRFI IHGFIDKGEE NWLSKICKNL FTVESVNCIC  120
VDWKSGSKTG YTQASQNIRI VGAEVAYFVE VLQSAFGYSP SNVHIGHSL GAHAAGEAGR  180
RINGTAGRIT GLDPAEPCFE GTPDLVRLDP SDALFVDVIH TDAAPIIPNM GFGMSQTVGH  240
LDFFPNGGKE MPGCQKNILS QIVDIDGIWE GTRDFVACNH LRSYKYYSDS ILNPDGFAGF  300
PCASYSVFSA NKCFPCPSEG CPQMGHYADR FPGKTNGVGQ IFYLNTGDAT NFARWRYKVA  360
VTLSGRKVTG HVLVTLFGNK GNSKQYEIFK GTLQPDSTHS NEFDSDVDVG DLQKVKFIWY  420
NRVINPTLPR VGASKIMVER NDGKVFNFCS QETVREDILL TLTPC                465
```

SEQ ID NO.3

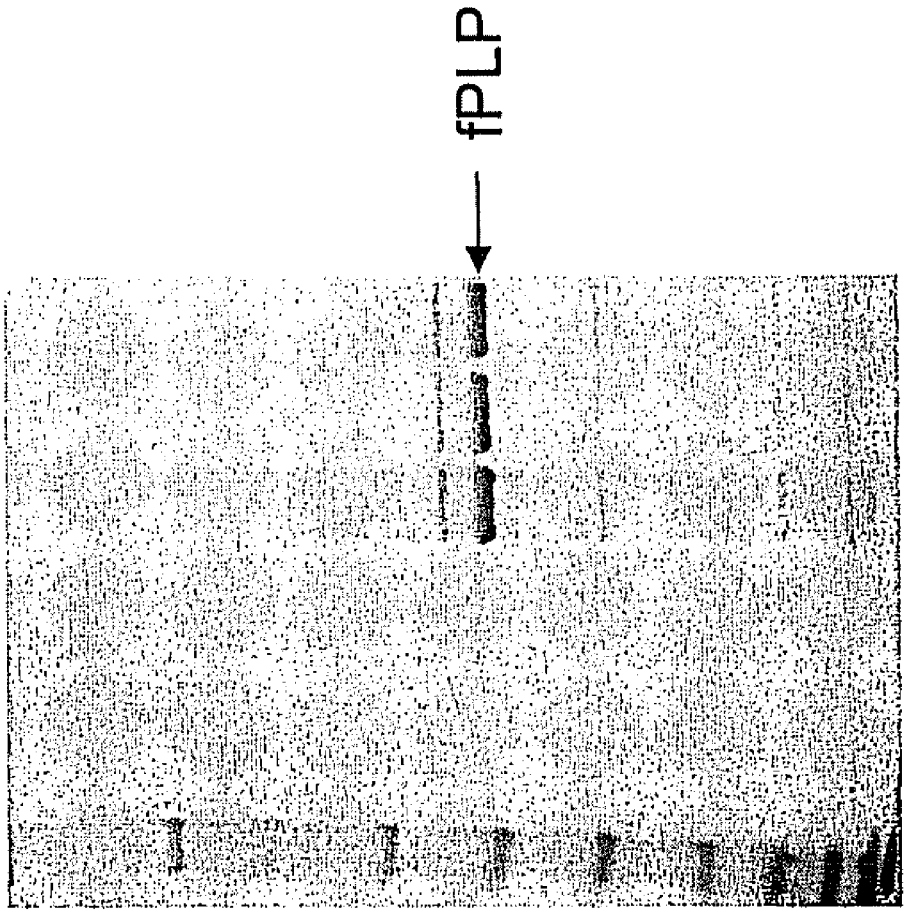

Comparison of detection sensitivity of fPLP monoclonal antibody with cPLP1 monoclonal antibody

Figure 9

```
Rat     (SEQ ID NO.: 12)  MLMLWTFAV-LLGAVAGKEVCFDKLGCFSDDAPWSGTIDRPLKALPWSPAQINTRFLLYT 59
Mouse   (SEQ ID NO.: 13)  MLMLWTFAV-LLGAVAGREVCFDKLGCFSDDAPWSGTLDRPLKALPWSPAQINTRFLLYT 59
Human   (SEQ ID NO.: 14)  MLPLWTLSL-LLGAVAGKEVCYERLGCFSDDSPWSGITERPLHILPWSPKDVNTRFLLYT 59
Feline  (SEQ ID NO.:  3)  MLLIWTLSL-LLGAVVGKEICFPRLGCFSDDAPWAGIAQRPLKILPWPPKDVNTRFLLYT 59
Horse   (SEQ ID NO.: 15)  ----WTLSL-LLGAVVGNEVCYERLGCFSDDSPWAGIVERPLKILPWSPEKVNTRFLLYT 55
Dog     (SEQ ID NO.: 16)  MVSIWTIALFLLGAAKAKEVCYEQIGCFSDAEPWAGTAIRPLKVLPWSPERIGTRFLLYT 60
                                         ***********************************************

Rat                       NENQDNYQKIT-SDASSIRNSNFKTNRKTRIIIHGFIDKGEENWLSDMCKNMFKVESVNC 118
Mouse                     NENPDNYQLIT-SDASNIRNSNFRTNRKTRIIIHGFIDKGEENWLSDMCKNMFRVESVNC 118
Human                     NENPNNFQEVA-ADSSSISGSNFKTNRKTRFIIHGFIDKGEENWLANVCKNLFKVESVNC 118
Feline                    NENPNNFEEII-ADESTIMSSNFNTDRKTRFIIHGFIDKGEENWLSKICKNLFTVESVNC 118
Horse                     NENPDNFQEIV-ADPSTIQSSNFNTGRKTRFIIHGFIDKGEESWLSTMCQNMFKVESVNC 114
Dog                       NKNPNNFQTLLPSDPSTIEASNFQTDKKTRFTIHGFINKGEENWLLDMCKNMFKVEEVNC 120
                                         ***********************************************

Rat                       ICVDWKGGSRATYTQATQNVRVVGAEVALLVNVLKSDLGHPPDNVHLIGHSLGSHVAGEA 178
Mouse                     ICVDWKGGSRTTYTQATQNVRVVGAEVALLVNVLQSDLGYSLNNVHLIGHSLGSHIAGEA 178
Human                     ICVDWKGGSRTGYTQASQNIRIVGAEVAYFVEFLQSAFGYSPSNVHVIGHSLGAHAAGEA 178
Feline                    ICVDWKSGSKTGYTQASQNIRIVGAEVAYFVEVLQSAFGYSPSNVHIIGHSLGAHAAGEA 178
Horse                     ICVDWKSGSRTAYSQASQNVRIVGAEVAYLVGVLQSSFDYSPSNVHIIGHSLGSHAAGEA 174
Dog                       ICVDWKKGSQTSYTQAANNVRVVGAQVAQMLSMLSANYSYSPSQVQLIGHSLGAHVAGEA 180
                                         ***********************************************

Rat                       GKRTFGAIGRITGLDAAEPYFQGTPEEVRLDPTDAQFVDAIHTDAAPIIPNLGFGMSQTV 238
Mouse                     GKRTFGAIGRITGLDPAEPYFQGTPEEVRLDPTDAQFVDAIHTDAGPIIPNLGFGMSQTV 238
Human                     GRRTNGTIGRITGLDPAEPCFQGTPELVRLDPSDAKFVDVIHTDGAPIVPNLGFGMSQVV 238
Feline                    GRRINGTAGRITGLDPAEPCFEGTPDLVRLDPSDALFVDVIHTDAAPIIPNMGFGMSQTV 238
Horse                     GRRTNGAVGRITGLDPAEPCFQGTPELVRLDPSDAQFVDVIHTDIAPFIPNLGFGMSQTA 234
Dog                       GSRTPG-LGRITGLDPVEASFQGTPEEVRLDPTDADFVDVIHTDAAPLIPFLGFGTSQQM 239
                                         ***********************************************

Rat                       GHLDFFPNGGMEMPGCQKNILSQIVDIDGIWEGTRDFAACNHLRSYKYYTDSIVNPTGFS 298
Mouse                     GHLDFFPNGGIEMPGCQKNILSQIVDIDGIWEGTRNFAACNHLRSYKFYTDSIVNPTGFA 298
Human                     GHLDFFPNGGVEMPGCKKNILSQIVDIDGIWEGTRDFAACNHLRSYKYYTDSIVNPDGFA 298
Feline                    GHLDFFPNGGKEMPGCQKNILSQIVDIDGIWEGTRDFVACNHLRSYKYYSDSILNPDGFA 298
Horse                     GHLDFFPNGGKEMPGCQKNVLSQIVDIDGIWQGTRDFAACNHLRSYKYYTDSILNPDGFA 294
Dog                       GHLDFFPNGGEEMPGCKKNALSQIVNLDGIWEGTRDFVACNHLRSYKYYSESILNPDGFA 299
                                         ***********************************************

Rat                       GFSCSSYNVFSANKCFPCGSEGCPQMGHYADKYPGKTKELYQKFYLNTGDKSNFARWRYQ 358
Mouse                     GFSCSSYSLFTANKCFPCGSGGCPQMGHYADRYPGKTSRLYQTFYLNTGDKSNFARWRYQ 358
Human                     GFPCASYNVFTANKCFPCPSGGCPQMGHYADRYPGKTNDVGQKFYLDTGDASNFARWRYK 358
Feline                    GFPCASYSVFSANKCFPCPSEGCPQMGHYADRFPGKTNGVGQIFYLNTGDATNFARWRYK 358
Horse                     GFSCASYSDFTANKCFPCSSEGCPQMGHYADRFPGRTKGVGQLFYLNTGDASNFARWRYR 354
Dog                       SYPCASYRAFESNKCFPCPDQGCPQMGHYADKFAVKTSDETQKYFLNTGDSSNFARWRYG 359
                                         ***********************************************

Rat                       VTVTLSGQKVTGHILVSLFGNGGNSKQYEVFKGSLHPGDTHVKEFDSDMDVGDLQKVKFI 418
Mouse                     VTVTLSGQKVTGHILVSLFGNGGNSKQYEVFKGSLQPGTSHVNEFDSDVDVGDLQKVKFI 418
Human                     VSVTLSGKKVTGHILVSLFGNKGNSKQYEIFKGTLKPDSTHSNEFDSDVDVGDLQMVKFI 418
Feline                    VAVTLSGRKVTGHVLVTLFGNKGNSKQYEIFKGTLQPDSTHSNEFDSDVDVGDLQKVKFI 418
Horse                     VDVTLSGKKVTGHVLVSLFGNKGNSRQYEIFQGTLKPDNTYSNEFDSDVEVGDLEKVKFI 414
Dog                       VSITLSGKRATGQAKVALFGSKGNTHQFNIFKGILKPGSTHSNEFDAKLDVGTIEKVKFL 419
                                         ***********************************************

Rat                       WYNNVINPTLPKVGASRISVERNDGR-VFNFCSQDTVREDVLLTLSAC 465
Mouse                     WYNNVINPTLPKVGASRITVERNDGR-VFNFCSQETVREDVLLTLSPC 465
Human                     WYNNVINPTLPRVGASKIIVETNVGK-QFNFCSPETVREEVLLTLTPC 465
Feline                    WYNRVINPTLPRVGASKIMVERNDGK-VFNFCSQETVREDILLTLTPC 465
Horse                     WYNNVINLTLPKVGASKITVERNDGS-VFNFCSEETVREDVLLTLTAC 461
Dog                       WNNNVVNPTFPKVGAAKITVQKGEEKTVHSFCSESTVREDVLLTLTPC 467
                                         ***********************************
```

FELINE PANCREATIC LIPASE

This application claims the benefit of priority to U.S. Provisional Application Ser. No. 60/980,029, filed Oct. 15, 2007, which is incorporated herein by reference in its entirety.

BACKGROUND OF THE INVENTION

1. Field of the Invention

The invention is related to the detection of pancreatic lipase. More specifically, the invention relates to feline pancreatic lipase polypeptides, polynucleotides encoding the polypeptides, antibodies specific for the polypeptides, methods for producing recombinant fPLP, methods of using the polypeptides and antibodies to detect pancreatic lipase in biological samples, and methods for diagnosing pancreatitis in an animal.

2. Description of Related Art

Lipases are water-soluble enzymes that hydrolyze water-insoluble substrates into more polar lipolysis products. Several lipases have been identified in microorganisms, plants, and animals (Lin, Y. H., Yu, C., Huang, A. H., 1986. Substrate specificities of lipases from corn and other seeds. Arch. Biochem. Biophys. 244, 346-356; Jaeger, K. E., Ransac, S., Dijkstra, B. W., Colson, C., van Heuvel, M., Misset, O., 1994. Bacterial lipases. FEMS Microbiology Reviews 15, 29-63; Petersen, S. B., Drablos, F., 1994. A sequence analysis of lipases, esterases, and related proteins. In: Woolley, P., Petersen, S. B. (Eds.), Lipases—their structure, biochemistry, and application, Cambridge University Press, Cambridge, pp. 23-48). Lipases share a common triad of amino acids (serine, aspartic or glutamic acid, and histidine) in the active site, which is also shared with serine proteases (Svendsen, A., 1994. Sequence comparisons within the lipase family. In: Woolley, P., Petersen, S. B. (Eds.), Lipases—their structure, biochemistry, and application, Cambridge University Press, Cambridge, pp. 1-21).

Another common feature of almost all lipases is glycosylation site motifs. Many lipases have been shown to be related phylogenetically. The pancreatic lipase gene family is a large gene family with 9 subfamilies (Petersen and Drablos, 1994; Carriere, F., Bezzine, S., Verger, R., 1997. Molecular evolution of the pancreatic lipase and two related enzymes towards different substrate selectivities. Journal of Molecular Catalysis B: Enzymatic 3, 55-64; Carriere, F., Withers-Martinez, C., Van Tilbeurgh, H., Roussel, A., Cambillau, C., Verger, R., 1998. Structural basis of the substrate selectivity of pancreatic lipases and some related proteins. Biochim. Biophys. Acta Rev. Biomembr. 1376, 417-432). In addition there are other groups of phylogenetically related lipases, and yet other lipases that do not belong to a defined gene family (Anderson, R. A., Sando, G. N., 1991. Cloning and expression of cDNA encoding human lysosomal acid lipase/cholesteryl ester hydrolase. Similarities to gastric and lingual lipases. J. Biol. Chem. 266, 22479-22484).

The main function of lipases is the hydrolysis of lipids. A lipase is needed whenever an apolar lipid needs to cross a biological membrane. Triglycerides are prime examples of apolar lipids. Thus lipase is needed in order for triglycerides to be absorbed from the intestinal tract. There are two digestive lipases in most vertebrate species, i.e., a preduodenal lipase and classical pancreatic lipase (Carriere, F., Gargouri, Y., Moreau, H., Ransac, S., Rogalska, E., Verger, R., 1994. Gastric lipases: cellular, biochemical and kinetic aspects. In: Woolley, P., Peterson, S. B. (Eds.), Lipases—their structure, biochemistry, and application, Cambridge University Press, Cambridge, pp. 181-205). Preduodenal lipase has been shown to originate from a single tissue in all species examined to date. A pharyngeal lipase was identified in cows and sheep, a lingual lipase in rats and mice, and a gastric lipase in human beings, monkeys, horses, pigs, guinea pigs, cats, and dogs. No preduodenal lipase could be identified in chickens. In human beings and dogs it has been shown that gastric lipase contributes significantly to the digestion of dietary triglycerides. However, pancreatic lipase (also called classical pancreatic lipase) is the most important enzyme in the digestion of dietary triglycerides (Carriere, F., Moreau, H., Raphel, V., Laugier, R., Benicourt, C., Junien, J.-L., Verger, R., 1991. Purification and biochemical characterization of dog gastric lipase. Eur. J. Biochem. 202, 75-83; Carriere, F., Barrowman, J. A., Verger, R., Laugier, R., 1993a. Secretion and contribution to lipolysis of gastric and pancreatic lipases during a test meal in humans. Gastroenterol. 105, 876-888).

It has recently been shown by immunolocalization that pancreatic lipase is detected only in pancreatic acinar cells in clinically healthy animals, suggesting that classical pancreatic lipase may be an ideal marker for function and pathology of the exocrine pancreas (Steiner, J. M., Berridge, B. R., Wojcieszyn, J., Williams, D. A., 2002. Cellular immunolocalization of gastric and pancreatic lipase in various tissues obtained from dogs. Am. J. Vet. Res. 63, 722-727). This hypothesis has been confirmed in clinical studies that have shown that the measurement of pancreatic lipase immunoreactivity in serum is a specific marker for exocrine pancreatic function and also highly sensitive for pancreatitis in the animals, such as dogs (Steiner, J. M., Broussard, J., Mansfield, C. S., Gumminger, S. R., Williams, D. A. 2001a. Serum canine pancreatic lipase immunoreactivity (cPLI) concentrations in dogs with spontaneous pancreatitis. J. Vet. Int. Med. 15, 274; Steiner, J. M., Gumminger, S. R., Rutz, G. M., Williams, D. A. 2000b. Serum canine pancreatic lipase immunoreactivity (cPLI) concentrations in dogs with exocrine pancreatic insufficiency. J. Vet. Int. Med. 15, 274; Steiner, J. M., Gumminger, S. R., Williams, D. A. 2000 c. Development and validation of an enzyme-linked immunosorbent assay (ELISA) for the measurement of canine pancreatic lipase immunoreactivity (cPLI) in serum. J. Vet. Int. Med. 15, 311).

Pancreatic lipase has an approximate molecular weight of 50 kilodaltons. The purification of classical pancreatic lipase has been reported in many species (Rathelot, J., Julien, R., Bosc-Bieme, I., Gargouri, Y., Canioni, P., Sarda, L., 1981. Horse pancreatic lipase. Interaction with colipase from various species. Biochimie 63, 227-234; Bosc-Bierne, I., Rathelot, J., Perrot, C., Sarda, L., 1984. Studies on chicken pancreatic lipase and colipase. Biochim. Biophys. Acta 794, 65-71; and U.S. Pat. No. 6,855,506).

Pancreatitis is a common condition in cats. Clinical symptoms of pancreatitis are non-specific and the disease can be difficult to diagnose. Thus, most cases remain undiagnosed. Pancreatitis is associated with an increased amount of digestive enzymes and zymogens leaking into the blood stream. One of these enzymes is pancreatic lipase. A number of assays have been developed to detect the presence of lipase in serum by use of catalytic assays. However, these assays lack sensitivity and specificity for pancreatic lipase in both human beings and animals. Lipase levels are affected by both pancreatic and non-pancreatic conditions such as kidney or liver diseases or administration of corticosteroids. Further, many cell types other than pancreatic cells also secret lipases. Thus, the changes in lipase activities do not necessarily reflect the presence of pancreatitis. What is desirable is reagents and a simple and rapid method for sensitive and specific detection of pancreatic lipase protein in a easily obtainable biological sample, without the need of taking biopsy samples and the use of immunohistochemistry.

The Applicants have previously developed an assay for detecting canine pancreatic lipase in a biological sample (copending application U.S. patent application Ser. No. 11/107,086, filed Apr. 15, 2005, published as U.S. Patent Application Publication No. 2005-0233368, which is incorporated herein by reference in its entirety). However, because of the innate differences existing between canine and feline, the levels of feline pancreatic lipase in the serum sample of a feline subject with sub-clinical and mild form of pancreatitis are much lower than those in canine. Thus, there exists a need for reagents specific for feline pancreatic lipase protein (fPLP) and a simple and sensitive method to enable accurate detection of fPLP and early diagnosis of feline diseases relating to fPLP.

SUMMARY OF THE INVENTION

In one aspect, the invention is directed to an isolated nucleic acid molecule having a nucleotide sequence encoding feline pancreatic lipase polypeptides (fPLP), allelic variants or fragments thereof. The invention includes vectors and host cells containing the sequences, and methods for expressing the polypeptides in the host cells.

The invention is also directed to monoclonal antibodies selected from the group consisting of FPL 17A.1D.12 and FPL2 35B.4B.1. The invention also provides for a cell line producing or secreting the monoclonal antibodies. In one embodiment, the invention provides for a cell line with an ATCC patent deposit number PTA-8506 or PTA-8507. The invention further provides for a monoclonal antibody that competes with the FPL 17A.1 D.12 and/or FPL2 35B.4B.1 for binding with feline pancreatic lipase.

Another aspect of the invention is directed to methods for determining the presence or amount of feline pancreatic lipase in a biological sample. The method includes using the monoclonal antibodies to specifically bind to feline pancreatic lipase polypeptides in the sample. The method includes using standards containing purified native or recombinant feline pancreatic lipase and comparing the levels of binding of the monoclonal antibody to the antigen in the standard with the binding in the sample in order to determine the presence and/or amount of the feline pancreatic lipase protein in the sample.

A further aspect of the invention is directed to methods for determining or diagnosing an animal subject, such as a feline subject, at risk for developing a condition relating to abnormal expression of feline pancreatic lipase protein. The abnormal expression may involve abnormal levels or abnormal pattern of expression of the protein in the animal. Such condition includes but is not limited to pancreatitis. In certain embodiments, the condition is identified by immunohistochemistry of tissue section from biopsy, and more preferably, by ELISA or similar types of immunoassay measuring the levels of fPLP in serum sample of the animal.

Further aspects of the invention are directed to devices and kits for performing methods for detecting and/or quantifying feline pancreatic lipase in biological samples.

BRIEF DESCRIPTION OF THE FIGURES

FIG. 1 depicts the primer design for the identification and amplification of feline pancreatic lipase. Shown are a series of degenerate primers for 3'RACE, 5'RACE, as well as primers designed for the amplification and subcloning of the feline pancreatic lipase gene. Specifically, RACE5 primer (SEQ ID NO:4) is the sense primer, designed based on alignments of published lipase sequences. See U.S. Patent Application Publication No. 2005-0233368. The designations for degenerate nucleotides are the following: r is A or G, y is C or T, h is A, C, or T, and v is A, C, or G. UPM primers (SEQ ID NO:5 and SEQ ID NO:6) are Universal Primer Mix for RACE amplification. Kc616 primer (SEQ ID NO:7) was designed based on sequence of feline pancreatic lipase gene obtained from 3' RACE experiment. Kc626 and Kc630 (SEQ ID NO:8 and SEQ ID NO:9) are primers for amplifying full length fPL PCR product. Fp1-4_xho1Stop and fpl_HindIII primers (SEQ ID NO:10 and SEQ ID NO:11) are designed for cloning the full length fPL gene as an XhoI/HindIII fragment into pBAC1.

FIG. 3 shows the cDNA sequence of the feline pancreatic lipase gene, designated fPL. (SEQ ID NO:2)

FIG. 4 shows the amino acid sequence of translated feline pancreatic lipase protein, designated fPLP (SEQ ID NO:3). The amino acid sequence was deduced from the cDNA sequence as identified by SEQ ID NO:2.

FIG. 5 shows a photograph of Coomassie-Blue stained SDS electrophoresis of recombinant fPLP purified from transfected SF9 cell culture in a representative experiment. Source of sample loaded in each lane is indicated as the following: Lane 1—clarified SF9 culture supernatant, volume 1.1 L, protein concentration 9.8 mg/ml, total protein 10,830 mg; lane 2—dialysate, volume 1.1 L, protein concentration 0.77 mg/ml, total protein 850 mg; lane 3—filtrate/load sample, volume 1.1 L, protein concentration 1.06 mg/ml, total protein 1,100 mg; lane 4—pooled fractions after SP column chromatography, volume 0.02 L, protein concentration 0.55 mg/ml, total protein 11 mg; lane 5-SP pool dialyzed, volume 0.02L, protein concentration 0.43 mg/ml, total protein 8.7 mg; and lane 6—final fPLP filtrate, volume 0.012 L, protein concentration 0.35 mg/ml, total protein 4.2 mg.

FIG. 9 shows an amino acid sequences alignment between pancreatic lipases from rat (Accession No. NP_037293) (SEQ ID NO:12), mouse (NP_081201) (SEQ ID NO:13), human (CAH72667) (SEQ ID NO:14), feline (SEQ ID NO:3), equine (CAA46961) (SEQ ID NO:15), and canine (NP_001003319) (SEQ ID NO:16).

DETAILED DESCRIPTION

Figure 2:
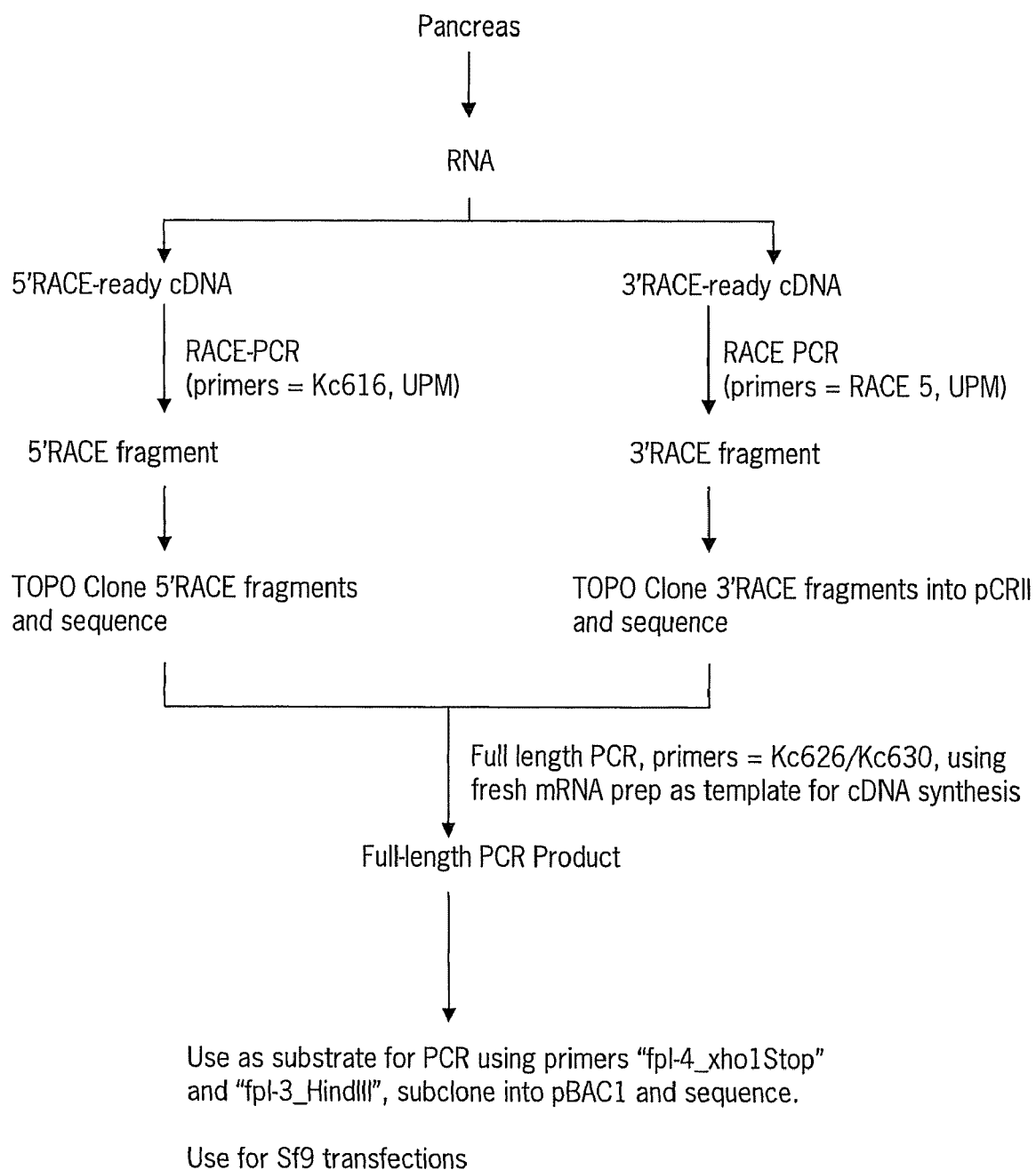
FIG. 2 shows a flow chart and schematic diagram of the cloning of full length fPL cDNA from pancreas RNA.

As used herein, the singular forms "a," "an", and "the" include plural referents unless the context clearly dictates otherwise.

The N-terminal amino acid sequence from purified feline pancreatic lipase has been reported (Steiner and Williams, U.S. Pat. No. 6,855,506):

KEIXaaFPRLGXaaFSDDA [SEQ ID NO:1]

Xaa indicates unknown amino acid residue. Based on this published amino acid sequence and on sequence similarities among pancreatic lipases of other species, a series of degenerate primers were designed and used for 3'RACE (Rapid Amplification of cDNA Ends) from which the complete 3' end of the gene was obtained. Similarly, 5'RACE was used to obtain the 5' end of the gene. The primers used for 3' and 5' RACE are shown in FIG. 1. The complete gene sequence (cDNA) and translated amino acid sequence is shown in FIGS. 3 and 4.

Accordingly, in one aspect the invention is directed to feline cDNA molecules (e.g. designated herein fPL, SEQ ID NO. 2), which encode feline lipase proteins such as feline pancreatic lipase protein or polypeptide (e.g. designated herein as fPLP, SEQ ID NO. 3), fPLP protein, fragments thereof, derivatives thereof, and variants thereof are collectively referred to herein as polypeptides of the invention or proteins of the invention.

Accordingly, in one aspect, the invention is directed to isolated nucleic acid molecules encoding polypeptides of the invention or biologically active portions thereof. The present invention provides nucleic acid sequences that encode protein molecules that have been identified as being members of the lipase family of proteins and are related to the pancreatic lipase subfamily (protein sequence is provided in FIG. 4, cDNA sequence is provided in FIG. 3). The peptide sequences provided in FIG. 4, as well as the obvious conservative amino acid substitutions and allelic variants will be referred herein as fPLP, the lipase peptides of the present invention, lipase peptides, or peptides/polypeptides/proteins of the present invention. The terms peptide, polypeptide and protein are used herein interchangeably.

In another aspect, the invention provides an isolated feline pancreatic lipase polypeptide having an amino acid sequence selected from the group consisting of (a) the amino acid sequence of SEQ ID NO:3, (b) an amino acid sequence of an allelic variant of SEQ ID NO:3, wherein the allelic variant is encoded by a nucleic acid that hybridizes under stringent conditions to the complementary strand of a nucleic acid molecule of SEQ ID NO:2, and (c) an antigenic fragment of an amino acid sequence of any of the polypeptide sequences of (a) or (b), wherein the fragment specifically binds to the feline pancreatic lipase monoclonal antibodies FPL 17A.1D.12 and/or FPL2 35B.4B.1.

The present invention provides isolated peptide, polypeptide, and protein molecules that consist of, consist essentially of, or comprise the amino acid sequences of the lipase peptides disclosed in the FIG. 4, (encoded by the nucleic acid molecule shown in FIG. 3), as well as all obvious variants of these peptides that are within the ability of one of skill in the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components.

In some uses, "substantially free of cellular material" includes preparations of the peptide having less than about 30% (by weight) other proteins (i.e., contaminating protein), less than about 20% other proteins, less than about 10% other proteins, or less than about 5% other proteins. When the peptide is recombinantly produced, it can also be substantially free of culture medium, or other components, i.e., less than about 40% (by weight), 30% or 20% of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the lipase peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated lipase peptide can be purified from cells or tissues that naturally express it, purified from cells that have been altered to express it (recombinant), or synthesized using known protein synthesis methods. For example, a nucleic acid molecule encoding the lipase peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 4 (SEQ ID NO:3), for example, proteins encoded by the cDNA nucleic acid sequences shown in FIG. 3 (SEQ ID NO:2). The amino acid sequence of such a protein is provided in FIG. 4. A protein consists of an amino acid sequence when the amino acid sequence is the final amino acid sequence of the protein.

The present invention further provides proteins that consist essentially of the amino acid sequences provided in FIG. 4 (SEQ ID NO:3), for example, proteins encoded by the cDNA nucleic acid sequences shown in FIG. 3 (SEQ ID NO:2). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 4 (SEQ ID NO:3), for example, proteins encoded by the cDNA nucleic acid sequences shown in FIG. 3 (SEQ ID NO:2). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the lipase peptides of the present invention are the naturally occurring mature proteins. A brief description of how various types of these proteins can be made/isolated is provided below.

The lipase peptides of the present invention can be attached to heterologous sequences to form chimeric or fusion proteins. Such chimeric or fusion proteins comprise a lipase peptide operatively linked to a heterologous protein having an amino acid sequence not substantially homologous to the lipase peptide. "Operatively linked" or "operably linked" indicates that the lipase peptide and the heterologous protein are fused in-frame. The heterologous protein can be fused, for example, to the N-terminus or C-terminus of the lipase peptide.

In some uses, the fusion protein does not affect the activity of the lipase peptide per se. For example, the fusion protein can include, but is not limited to, enzymatic fusion proteins, for example beta-galactosidase fusions, yeast two-hybrid GAL fusions, poly-His fusions, MYC-tagged, His-tagged and Ig fusions. Such fusion proteins, particularly poly-His fusions, can facilitate the purification of recombinant lipase peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., Current Protocols in Molecular Biology, 1992). Moreover, many expression vectors are commercially available that already encode a fusion moiety (e.g., a GST protein). A lipase peptide-encoding nucleic acid can be cloned into such an expression vector such that the fusion moiety is linked in-frame to the lipase peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the lipase peptides of the present invention. The degree of homology/identity present will be based primarily on whether the peptide is a functional variant or non-functional variant, and the amount of divergence present in the paralog family.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, 90%, or 95% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). In a preferred embodiment, the percent identity between two amino acid sequences is determined using the Needleman and Wunsch (J. Mol. Biol. (48): 444-453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al, Nucleic Acids Res. 12(1):387 (1984)) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11-17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (J. Mol. Biol. 215: 403-10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (Nucleic Acids Res. 25(17):3389-3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the lipase peptides of the present invention as well as being encoded by the same genetic locus as the lipase peptide provided herein.

Allelic variants of a lipase peptide can readily be identified as being a feline protein having a high degree (significant) of sequence homology/identity to at least a portion of the lipase peptide as well as being encoded by the same genetic locus as the lipase peptide provided herein. As used herein, two proteins (or a region of the proteins) have significant homology when the amino acid sequences are typically at least about 70-80%, 80-90%, and more typically at least about 90-95% or more homologous. In preferred embodiments, the variant of the fPLP shares at least 85%, at least 90% or at least 95% amino acid sequence homology with the fPLP identified by SEQ ID NO:3. A significantly homologous amino acid sequence, according to the present invention, will be encoded by a nucleic acid sequence that will hybridize to a lipase peptide encoding nucleic acid molecule under stringent conditions as more fully described below.

Paralogs of a lipase peptide can readily be identified as having some degree of significant sequence homology/identity to at least a portion of the lipase peptide, as being encoded by a gene from felines, and as having similar activity or function. Two proteins will typically be considered paralogs when the amino acid sequences are typically at least about 60%, or greater, and more typically at least about 70% or greater homology through a given region or domain. Such paralogs will be encoded by a nucleic acid sequence that will hybridize to a lipase peptide encoding nucleic acid molecule under moderate to stringent conditions as more fully described below.

Non-naturally occurring variants of the lipase peptides of the present invention can readily be generated using recombinant techniques. Such variants include, but are not limited to deletions, additions and substitutions in the amino acid sequence of the lipase peptide. For example, one class of substitutions is conserved amino acid substitution. Such substitutions are those that substitute a given amino acid in a lipase peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., Science 247:1306-1310 (1990). Other commonly known conservative amino acid substitutions are shown in the following table.

TABLE 1

Amino Acid Substitutions

| Original Residues | Exemplary Substitutions | Preferred Substitutions |
| --- | --- | --- |
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

In certain embodiments, the invention provides fPLP variants that have one or more amino acid substitutions in regions that are not highly conserved among pancreatic lipases isolated from different species. An amino acid sequence alignment of pancreatic lipase from different species is shown in FIG. 9.

Variant lipase peptides can be fully functional or can lack function in one or more activities, e.g. ability to bind substrate, ability to hydrolyze substrate, etc. Fully functional variants typically contain only conservative variation or variation in non-critical residues or in non-critical regions. Functional variants can also contain substitution of similar amino acids that result in no change or an insignificant change in function. Alternatively, such substitutions may positively or negatively affect function to some degree.

Amino acids that are essential for function can be identified by methods known in the art, such as site-directed mutagenesis or alanine-scanning mutagenesis (Cunningham et al., Science 244:1081-1085 (1989)). The latter procedure introduces single alanine mutations at every residue in the molecule. The resulting mutant molecules are then tested for biological activity such as lipase activity or in assays such as an in vitro proliferative activity. Sites that are critical for binding partner/substrate binding can also be determined by structural analysis such as crystallization, nuclear magnetic resonance or photoaffinity labeling (Smith et al., J. Mol. Biol. 224:899-904 (1992); de Vos et al. Science 255:306-312 (1992)).

The present invention further provides fragments of the lipase peptides, in addition to proteins and peptides that comprise and consist of such fragments. The term "fragment" as used herein refers to a peptide or polypeptide sequence that is shorter than the full length sequence as identified in SEQ ID NO:3. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a lipase peptide. Such fragments can be chosen based on the ability to retain one or more of the biological activities of the lipase peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the lipase peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis).

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in lipase peptides are described in basic texts, detailed monographs, and the research literature, and they are well known to those of skill in the art.

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as Proteins—Structure and Molecular Properties, 2nd Ed., T. E. Creighton, W. H. Freeman and Company, New York (1993). Many detailed reviews are available on this subject, such as by Wold, F., Posttranslational Covalent Modification of Proteins, B. C. Johnson, Ed., Academic Press, New York 1-12 (1983); Seifter et al. (Meth. Enzymol. 182: 626-646 (1990)) and Rattan et al. (Ann. N.Y. Acad. Sci. 663:48-62 (1992)).

Accordingly, the lipase peptides of the present invention also encompass derivatives or analogs in which a substituted amino acid residue is not one encoded by the genetic code, in which a substituent group is included, in which the mature lipase peptide is fused with another compound, such as a compound to increase the half-life of the lipase peptide (for example, polyethylene glycol), or in which the additional amino acids are fused to the mature lipase peptide, such as a leader or secretory sequence or a sequence for purification of the mature lipase peptide or a pro-protein sequence.

Antibodies

The invention also provides antibodies that selectively bind to one of the peptides of the present invention, a protein comprising such a peptide, as well as variants and fragments thereof. In one aspect, the invention is directed to monoclonal antibodies selected from the group consisting of FPL 17A.1D.12 and FPL2 35B.4B.1. In another aspect, the monoclonal antibody specifically binds to the feline pancreatic lipase protein. As used herein, an antibody specifically or selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with what is recognized within the art: they are multi-subunit proteins produced by a mammalian organism in response to an antigen challenge. The term "antibody" includes, but is not limited to, both naturally occurring and non-naturally occurring antibodies. As used herein, the term "antibody" is intended to refer broadly to any immunologic binding agent such as IgG, IgM, IgA, IgD and IgE. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide or DNA encoding the peptide is used as an immunogen and is administered to a mammalian organism, such as a rat, rabbit or mouse. The full-length protein, an antigenic peptide fragment or a fusion protein can be used as antigens. Particularly important fragments are those covering functional domains, and domain of sequence homology or divergence amongst the family, such as those that can readily be identified using protein alignment methods. Fragments that are unique to a particular member of the family are of interest for generating antibody specific for the member.

Antibodies are preferably prepared from regions or discrete fragments of the lipase proteins. Antibodies can be prepared from any region of the peptide as described herein. However, preferred regions will include those involved in function/activity and/or lipase/binding partner interaction.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness.

In one aspect, the antibodies of the invention are monoclonal antibodies produced by a mouse hybridoma cell line. This cell line can be made by fusing a mouse myeloma cell line with the spleen cells from mice that have been injected with the complete feline pancreatic lipase protein, or antigenic portions thereof. Any one of a number of myeloma cells may be used, as is known by one of skill in the art. Available murine myeloma lines, such as those from the American Type Culture Collection (ATCC), 10801 University Boulevard, Manassas, Va., 20110-2209, may be used in the generation of hybridoma cell line. As more completely described in the Examples below, the hybridoma cell lines of the invention have been deposited with the American Tissue Culture Collection on Jun. 26, 2007. These cell lines have been assigned Patent Deposit Numbers PTA-8506 and PTA-8507. The deposits will be maintained under the terms of the Budapest Treaty on the International Recognition of the Deposit of Microorganisms. The deposits are provided as a convenience to those of skill in the art and are not an admission that the deposit is required under 35 U.S.C. §112. The antibodies secreted from the cell lines with the deposit number PTA-8506 and PTA-8507 have been designated FPL 17A.1D.12 and FPL2 35B.4B.1, respectively. The invention in one aspect provides fPLP monoclonal antibodies FPL 17A.1D.12 and FPL2 35B.4B.1. In another aspect, the invention provides a monoclonal antibody that competes with FPL 17A.1D.12 and/or FPL2 35B.4B.1 for binding to feline pancreatic lipase protein. In yet another aspect, the invention provides cell lines with deposit numbers PTA-8506 and PTA-8507. Throughout the description, the antibody designations FPL 17A.1D.12 and FPL2 35B.4B.1 may be used interchangeably with PTA-8506 and PTA 8507, respectively.

Polyclonal antibodies to feline pancreatic lipase have been described by Steiner et al. (U.S. Pat. No. 6,855,506, which is incorporated herein in its entirety). However, monoclonal antibodies of the claimed invention exhibit greater specificity for fPLP. Further, the monoclonal antibodies produced by hybridoma cell lines exhibit less variability and more reproducibility than those seen in polyclonal antibodies produced from different bleeding from one animal or from different animals.

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells, tissues or fluids to determine the pattern of expression of the protein among various tissues in an organism and over the course of normal development. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition related to abnormal expression of fPLP. Additionally, such antibodies can be used to measure the level of the fPLP in a biological sample, such as serum sample, for determination or diagnosis of a certain condition. Particularly, the condition is feline pancreatitis. Antibody detection of circulating fragments of the full length protein can be used to identify turnover of the full length protein.

Further, the antibodies can be used to assess disease states such as in active stages of the disease or in subclinical stage of the disease. The antibodies can also be used to assess an individual's predisposition toward certain diseases. When a disorder is caused by an inappropriate tissue distribution of the protein, incorrect developmental expression of the protein, abnormal levels of expression of the protein, or abnormally processed protein, the antibody prepared against the normal protein can be used to detect and diagnose the disorder. If a disorder is characterized by a specific mutation in the protein, antibodies specific for this mutant protein can be used to assay for the presence of the specific mutant protein.

Polynucleotides

The invention provides isolated polynucleotides encoding the feline pancreatic lipase protein. The term "lipase polynucleotide" or "lipase nucleic acid" includes the sequence shown in SEQ ID NO:2, as well as variants and fragments of the lipase polynucleotide.

An "isolated" lipase nucleic acid is one that is separated from other nucleic acid present in the natural source of the lipase nucleic acid. Preferably, an "isolated" nucleic acid is free of sequences which naturally flank the lipase nucleic acid sequence (i.e., sequences located upstream (at the 5' end) and downstream (at the 3' ends) of the lipase nucleic acid sequence) in the genomic DNA of the organism from which the nucleic acid is derived. However, there can be some flanking nucleotide sequences, for example up to about 5 Kb. The important point is that the lipase nucleic acid is isolated from flanking sequences such that it can be subjected to the specific manipulations described herein, such as recombinant expression, preparation of probes and primers, and other uses specific to the lipase nucleic acid sequences.

Moreover, an "isolated" nucleic acid molecule, such as a cDNA or RNA molecule, can be substantially free of other cellular material, or culture medium when produced by recombinant techniques, or chemical precursors or other chemical reagents when chemically synthesized. However, the nucleic acid molecule can be fused to other coding or regulatory sequences and still be considered isolated.

In some instances, the isolated material will form part of a composition (for example, a crude extract containing other substances), buffer system or reagent mix. In other circumstances, the material may be purified to essential homogeneity, for example as determined by PAGE or column chromatography such as HPLC. Preferably, an isolated nucleic acid comprises at least about 50, 80 or 90% (on a molar basis) of all macromolecular species present.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

The lipase polynucleotides can encode the mature protein plus additional amino or carboxy-terminal amino acids, or amino acids interior to the mature polypeptide (when the mature form has more than one polypeptide chain, for instance). Such sequences may play a role in processing of a protein from precursor to a mature form, facilitating protein trafficking, prolonging or shortening protein half-life or facilitating manipulation of a protein for assay or production, among other things. The additional amino acids may be processed away from the mature protein by enzymatic activities.

The lipase polynucleotides include, but are not limited to, the sequence encoding the mature polypeptide alone, the sequence encoding the mature polypeptide and additional coding sequences, such as a leader or secretory sequence (e.g., a pre-pro or pro-protein sequence), the sequence encoding the mature polypeptide, with or without the additional coding sequences, plus additional non-coding sequences, for example introns and non-coding 5' and 3' sequences such as transcribed but non-translated sequences that may play a role in transcription, mRNA processing (including splicing and polyadenylation signals), ribosome binding and stability of mRNA. In addition, the polynucleotide may be fused to a marker sequence encoding, for example, a peptide that facilitates purification. Such purification facilitating peptides are well known to one of skill in the art, including but not limited to His tag, and a GST protein moiety.

Lipase polynucleotides can be in the form of RNA, such as mRNA, or in the form of DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (opposite or anti-sense strand).

Lipase nucleic acid can comprise the nucleotide sequence shown in SEQ ID NO:2, corresponding to feline cDNA. In one embodiment, the lipase nucleic acid comprises only the coding region.

The invention further provides variant lipase polynucleotides, and fragments thereof, that differ from the nucleotide sequence shown in SEQ ID NO:2 due to degeneracy of the genetic code and thus encode the same protein as that encoded by the nucleotide sequence shown in SEQ ID NO:2.

The invention also provides lipase nucleic acid molecules encoding the variant polypeptides described herein. Such polynucleotides may be naturally occurring, such as allelic variants (same locus), homologs (different locus) or may be constructed by recombinant DNA methods or by chemical synthesis. Such non-naturally occurring variants may be made by mutagenesis techniques, including those applied to polynucleotides, cells, or organisms. Accordingly, as discussed above, the variants can contain nucleotide substitutions, deletions, inversions and insertions.

Typically, variants have a substantial identity with a nucleic acid molecule of SEQ ID NO:2 and the complements thereof. Variation can occur in either or both the coding and non-coding regions. The variations can include both conservative and non-conservative amino acid substitutions. Homologs, and allelic variants can be identified using methods well known in the art. These variants comprise a nucleotide sequence encoding a lipase that is at least about 60-65%, 65-70%, typically at least about 70-75%, more typically at least about 80-85%, and most typically at least about 90-95% or more homologous to the nucleotide sequence shown in SEQ ID NO:2. Such nucleic acid molecules can readily be identified as being able to hybridize under stringent conditions, to the nucleotide sequence shown in SEQ ID NO:2 or a fragment of the sequence. It is understood that stringent hybridization does not indicate substantial homology where it is due to general homology, such as poly A sequences, or sequences common to all or most proteins or all lipase enzymes. Moreover, it is understood that variants do not include any of the nucleic acid sequences that may have been disclosed prior to the invention.

As used herein, the term "hybridizes under stringent conditions" is intended to describe conditions for hybridization and washing under which nucleotide sequences encoding a polypeptide at least about 60-65% homologous to each other typically remain hybridized to each other. The conditions can be such that sequences at least about 65%, at least about 70%, at least about 75%, at least about 80%, at least about 85%, at least about 90%, or at least about 95% or more identical to each other remain hybridized to one another. Such stringent conditions are known to those skilled in the art and can be found in Current Protocols in Molecular Biology, John Wiley & Sons, N.Y. (1989), 6.3.1-6.3.6, incorporated by reference. One non-limiting example of stringent hybridization conditions are hybridization in 6× sodium chloride/sodium citrate (SSC) at about 45° C., followed by one or more washes in 0.2×SSC, 0.1% SDS at 50-65° C. In another non-limiting example, nucleic acid molecules are allowed to hybridize in 6× sodium chloride/sodium citrate (SSC) at about 45° C., followed by one or more low stringency washes in 0.2×SSC/ 0.1% SDS at room temperature, or by one or more moderate stringency washes in 0.2×SSC/0.1% SDS at 42° C., or washed in 0.2×SSC/0.1% SDS at 65° C. for high stringency. In one embodiment, an isolated nucleic acid molecule that hybridizes under stringent conditions to the sequence of SEQ ID NO:2 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein). In another embodiment, an isolated nucleic acid molecule that hybridizes under stringent conditions to the sequence of SEQ ID NO:2 corresponds to recombinant nucleic acid molecule that does not occur in nature.

As understood as routine practice by those of ordinary skill in the art, the exact conditions can be determined empirically and depend on ionic strength, temperature and the concentration of destabilizing agents such as formamide or denaturing agents such as SDS. Other factors considered in determining the desired hybridization conditions include the length of the nucleic acid sequences, base composition, percent mismatch between the hybridizing sequences and the frequency of occurrence of subsets of the sequences within other non-identical sequences. Thus, equivalent conditions can be determined by varying one or more of these parameters while maintaining a similar degree of identity or similarity between the two nucleic acid molecules.

The present invention also provides isolated nucleic acids that contain a single or double stranded fragment or portion that hybridizes under stringent conditions to the nucleotide sequence of SEQ ID NO:2 or the complement of SEQ ID NO:2. In one embodiment, the nucleic acid consists of a portion of the nucleotide sequence of SEQ ID NO:2 or the complement of SEQ ID NO:2.

It is understood that isolated fragments include any contiguous sequence not disclosed prior to the invention as well as sequences that are substantially the same and which are not disclosed. Accordingly, if a fragment is disclosed prior to the present invention, that fragment is not intended to be encompassed by the invention. When a sequence is not disclosed prior to the present invention, an isolated nucleic acid fragment is at least about 6, preferably at least about 10, 13, 18, 20, 23 or 25 nucleotides, and can be 30, 40, 50, 100, 200, 500 or more nucleotides in length. Longer fragments, for example, 30 or more nucleotides in length, which encode antigenic proteins or polypeptides described herein are useful.

Furthermore, the invention provides polynucleotides that comprise a fragment of the full-length lipase polynucleotides. The fragment can be single or double-stranded and can comprise DNA or RNA. The fragment can be derived from either the coding or the non-coding sequence. In another embodiment an isolated lipase nucleic acid encodes the entire coding region.

Thus, lipase nucleic acid fragments further include sequences corresponding to the domains, subregions, and specific functional sites as described herein. A person of ordinary skill in the art would be aware of the many permutations that are possible.

Where the location of the domains or sites have been predicted by computer analysis, one of ordinary sill would appreciate that the amino acid residues constituting these domains can vary depending on the criteria used to define the domains. However, it is understood that a lipase fragment includes any nucleic acid sequence that does not include the entire gene. The invention also provides lipase nucleic acid fragments that encode epitope bearing regions of the lipase proteins described herein. Nucleic acid fragments, according to the present invention, are not to be construed as encompassing those fragments that may have been disclosed prior to the invention.

The nucleic acid fragments of the invention provide probes or primers in assays such as those described below. "Probes" are oligonucleotides that hybridize in a base-specific manner to a complementary strand of nucleic acid. Such probes include polypeptide nucleic acids, as described in Nielsen et al. (1991) Science 254:1497-1500. Typically, a probe comprises a region of nucleotide sequence that hybridizes under highly stringent conditions to at least about 15, typically about 20-25, and more typically about 40, 50 or 75 consecutive nucleotides of the nucleic acid sequence shown in SEQ ID NO:2 and the complements thereof. More typically, the probe further comprises a label, e.g., radioisotope, fluorescent compound, enzyme, or enzyme co-factor.

As used herein, the term "primer" refers to a single-stranded oligonucleotide which acts as a point of initiation of template-directed DNA synthesis using well-known methods (e.g., PCR, LCR) including, but not limited to those described herein. The appropriate length of the primer depends on the particular use, but typically ranges from about 15 to 100 nucleotides, preferably from about 15 to 30. In certain experiment, the primer length can be longer. One of skill in the art would be able to design optimal length of primer for a particular use. The term "primer site" refers to the area of the target DNA to which a primer hybridizes. The term "primer pair" refers to a set of primers including a 5' (upstream) primer that hybridizes with the 5' end of the nucleic acid sequence to be amplified and a 3' (downstream) primer that hybridizes with the complement of the sequence to be amplified.

Where the polynucleotides are used to assess lipase properties or functions, such as in the assays described herein, all or less than all of the entire cDNA can be useful. Assays specifically directed to lipase functions, such as assessing agonist or antagonist activity, encompass the use of known fragments. Further, diagnostic methods for assessing lipase function can also be practiced with any fragment, including those fragments that may have been known prior to the invention. Similarly, in methods involving treatment of lipase dysfunction, all fragments are encompassed including those, which may have been known in the art.

The lipase polynucleotides are useful as a hybridization probe for cDNA and genomic DNA to isolate a full-length cDNA and genomic clones encoding the polypeptide described in SEQ ID NO:3 and to isolate cDNA and genomic clones that correspond to variants producing the same polypeptide shown in SEQ ID NO:3 or the other variants described herein. Variants can be isolated from the same tissue and organism from which the polypeptide shown in SEQ ID NO:3 were isolated, different tissues from the same organism, or from different organisms. This method is useful for isolating genes and cDNA that are developmentally-controlled and therefore may be expressed in the same tissue or different tissues at different points in the development of an organism.

The probe can correspond to any sequence along the entire length of the gene encoding the lipase. Accordingly, it could be derived from 5' noncoding regions, the coding region, and 3' noncoding regions. The nucleic acid probe can be, for example, the full-length cDNA of SEQ ID NO:2 or a fragment thereof that is sufficient to specifically hybridize under stringent conditions to mRNA or DNA.

The lipase polynucleotides are also useful for constructing recombinant vectors. Such vectors include expression vectors that express a portion of, or all of, the lipase polypeptides. Vectors also include insertion vectors, used to integrate into another polynucleotide sequence, such as into the cellular genome, to alter in situ expression of lipase genes and gene products. For example, an endogenous lipase coding sequence can be replaced via homologous recombination with all or part of the coding region containing one or more specifically introduced mutations. The lipase polynucleotides are also useful for expressing antigenic portions of the lipase proteins. The lipase polynucleotides are also useful for making vectors that express part, or all, of the lipase polypeptides. The lipase polynucleotides are also useful as hybridization probes for determining the level of lipase nucleic acid expression. Accordingly, the probes can be used to detect the presence of, or to determine levels of, lipase nucleic acid in cells, tissues, and in organisms. The nucleic acid whose level is determined can be DNA or RNA. Accordingly, probes corresponding to the polypeptides described herein can be used to assess gene copy number in a given cell, tissue, or organism. This is particularly relevant in cases in which there has been an amplification of the lipase genes.

Vectors/Host Cells

The invention also provides vectors containing the lipase polynucleotides. The polynucleotides can be cloned into the vector using molecular cloning techniques well known in the art, for example, as described in Sambrook et al. (1989) Molecular Cloning: A Laboratory Manual 2nd. ed., Cold Spring Harbor Laboratory Press, Cold Spring Harbor, N.Y. (incorporated herein in its entirety for any purpose). The term "vector" refers to a vehicle, preferably a nucleic acid molecule that can transport the lipase polynucleotides. When the vector is a nucleic acid molecule, the lipase polynucleotides are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC. The vector may or may not contain a promoter sequence.

A vector can be maintained in the host cell as an extrachromosomal element where it replicates and produces additional copies of the lipase polynucleotides. Alternatively, the vector may integrate into the host cell genome and produce additional copies of the lipase polynucleotides when the host cell replicates.

The invention provides vectors for the maintenance (cloning vectors) or vectors for expression (expression vectors) of the lipase polynucleotides. The vectors can function in prokaryotic or eukaryotic cells or in both (shuttle vectors).

Expression vectors contain cis-acting regulatory regions that are operably linked in the vector to the lipase polynucleotides such that transcription of the polynucleotides is allowed in a host cell. The polynucleotides can be introduced into the host cell with a separate polynucleotide capable of affecting transcription. Thus, the second polynucleotide may provide a trans-acting factor interacting with the cis-regulatory control region to allow transcription of the lipase polynucleotides from the vector. Alternatively, a trans-acting factor may be supplied by the host cell. Finally, a trans-acting factor can be produced from the vector itself.

It is understood, however, that in some embodiments, transcription and/or translation of the lipase polynucleotides can occur in a cell-free system.

The regulatory sequence to which the polynucleotides described herein can be operably linked include promoters for directing mRNA transcription. These include, but are not limited to, the left promoter from bacteriophage lambda, the lac, TRP, and TAC promoters from E. coli, the early and late promoters from SV40, the CMV immediate early promoter, the adenovirus early and late promoters, bacteriophage T3 or T7 promoter, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al. (1989) Molecular Cloning: A Laboratory Manual 2nd. ed., Cold Spring Harbor Laboratory Press, Cold Spring Harbor, N.Y.).

A variety of expression vectors can be used to express a lipase polynucleotide. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al. (1989) Molecular Cloning: A Laboratory Manual 2nd. ed., Cold Spring Harbor Laboratory Press, Cold Spring Harbor, N.Y.

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The lipase polynucleotides can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate polynucleotide can be introduced into an appropriate host cell for propagation or expression using well-known techniques. Bacterial cells include, but are not limited to, *E. coli, Streptomyces*, and *Salmonella typhimurium*. Eukaryotic cells include, but are not limited to, yeast, insect cells such as *Drosophila*, animal cells such as COS and CHO cells, and plant cells.

As described herein, it may be desirable to express the polypeptide as a fusion protein. Accordingly, the invention provides fusion vectors that allow for the production of the lipase polypeptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired polypeptide can ultimately be separated from the fusion moiety. Proteolytic enzymes include, but are not limited to, factor Xa, thrombin, and enterokinase. Typical fusion expression vectors include pGEX (Smith et al. (1988) Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al. (1988) Gene 69:301-315) and pET 11d (Studier et al. (1990) Gene Expression Technology: Methods in Enzymology 185:60-89).

Recombinant protein expression can be maximized in host bacteria cells by providing a genetic background wherein the host cell has an impaired capacity to proteolytically cleave the recombinant protein. (Gottesman, S. (1990) Gene Expression Technology: Methods in Enzymology 185, Academic Press, San Diego, Calif. 119-128). Alternatively, the sequence of the polynucleotide of interest can be altered to provide preferential codon usage for a specific host cell, for example *E. coli*. (Wada et al. (1992) Nucleic Acids Res. 20:2111-2118).

The lipase polynucleotides can also be expressed by expression vectors that are operative in yeast. Examples of vectors for expression in yeast e.g., *S. cerevisiae* include pYepSec1 (Baldari et al. (1987) EMBO J. 6:229-234), pMFa (Kujan et al. (1982) Cell 30:933-943), pJRY88 (Schultz et al. (1987) Gene 54:113-123), and pYES2 (Invitrogen Corporation, San Diego, Calif.).

The lipase polynucleotides can also be expressed in insect cells using, for example, baculovirus expression vectors. Baculovirus vectors available for expression of proteins in cultured insect cells (e.g., Sf9 and Sf21 cells) include the pAc series (Smith et al. (1983) Mol. Cell. Biol. 3:2156-2165) and the pVL series (Lucklow et al. (1989) Virology 170:31-39).

In certain embodiments of the invention, the polypeptides described herein are expressed in mammalian cells using mammalian expression vectors. Examples of mammalian expression vectors include pCDM8 (Seed, B. (1987) Nature 329:840), pMT2PC (Kauffman et al. (1987) EMBO J. 6:187-195). The polypeptide of the invention can be transiently expressed in the cell transfected with the expression vector. Alternatively, once the expression vector polynucleotide is integrated into the cell genome, the polypeptide of the invention can be stably expressed in the cell.

The expression vectors listed herein are provided by way of example only of the well-known vectors available to those of ordinary skill in the art that would be useful to express the lipase polynucleotides. The person of ordinary skill in the art would be aware of other vectors suitable for maintenance, propagation, or expression of the polynucleotides described herein. These are found for example in Sambrook et al. (1989) Molecular Cloning: A Laboratory Manual 2nd, ed., Cold Spring Harbor Laboratory, Cold Spring Harbor Laboratory Press, Cold Spring Harbor, N.Y.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the polynucleotide sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook et al. (Molecular Cloning: A Laboratory Manual, 2d ed., Cold Spring Harbor Laboratory, Cold Spring Harbor Laboratory=Press, Cold Spring Harbor, N.Y.).

Host cells can contain more than one vector. Thus, different nucleotide sequences can be introduced on different vectors of the same cell. Similarly, the lipase polynucleotides can be introduced either alone or with other polynucleotides that are not related to the lipase polynucleotides such as those providing trans-acting factors for expression vectors. When more than one vector is introduced into a cell, the vectors can be introduced independently, co-introduced or joined to the lipase polynucleotide vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the polynucleotides described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the polypeptide is desired, appropriate secretion signals are incorporated into the vector. The signal sequence can be endogenous to the lipase polypeptides or heterologous to these polypeptides.

Where the polypeptide is not secreted into the medium, the protein can be isolated from the host cell by standard disruption procedures, including freeze thaw, sonication, mechanical disruption, use of lysing agents and the like. The polypeptide can then be recovered and purified by well-known purification methods including ammonium sulfate precipitation, acid extraction, anionic or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the polypeptides described herein, the polypeptides can have various glycosylation patterns, depending upon the cell, or maybe non-glycosylated as when produced in bacteria. In addition, the polypeptides may include an initial modified methionine in some cases as a result of a host-mediated process.

It is understood that "host cells" and "recombinant host cells" refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

Exemplary antigenic and enzymatic characteristics of fPLP which are exhibited by such polypeptides include lipase activity, ability to bind with molecules with which fPLP is able to bind, and ability to induce production of antibody substances which bind specifically with an epitope which occurs at or near the surface of the fPLP protein. The polypeptides of the invention, or biologically active portions thereof, can be operably linked with a heterologous amino acid sequence to form fusion proteins. In addition, one or more polypeptides of the invention or biologically active portions thereof can be incorporated into pharmaceutical compositions, which can optionally include pharmaceutically acceptable carriers. Such pharmaceutical compositions can be used to treat or prevent one or more of the disorders identified herein. The invention encompasses antibody substances that specifically bind with a polypeptide of the invention including, for example, fPLP and fragments thereof. Exemplary antibody substances that are included within the scope of the invention are monoclonal and polyclonal antibodies, antibody fragments, single-chain antibodies, cell free antibodies, and cell-surface-bound antibodies, and T cell receptors. These antibody substances can be made, for example, by providing the polypeptide of the invention to an immunocompetent vertebrate and thereafter harvesting blood or serum from the vertebrate. Antibody substances can, alternatively, be generated by screening a library of phage to identify phage particles that display a subunit, which binds with fPLP or an epitope thereof.

In another aspect, the invention provides methods for detecting activity or expression of a polypeptide of the invention in a biological sample by contacting the biological sample with an agent capable of detecting such activity (e.g., a labeled substrate or another compound that can be detected after being acted upon by an active polypeptide of the invention), with an agent which binds specifically with a polypeptide of the invention (e.g., an antibody substance of the invention), or with an agent for detecting production of an RNA encoding a polypeptide of the invention (e.g., a reverse transcriptase primer complementary to a portion of an mRNA encoding the polypeptide).

Method for Detecting Feline Pancreatic Lipase Protein

In one aspect, the invention is directed to an immunological method for detecting the presence or amount of feline pancreatic lipase in a biological sample. The invention provides methods, devices and kits that use one or more feline lipase monoclonal antibodies. In another aspect, the method includes calibrators and standards comprising one or more feline pancreatic lipase polypeptides.

In one embodiment of the invention, the method for determining the presence or amount of feline pancreatic lipase polypeptide (fPLP) in a biological sample comprises the steps of (a) contacting the sample with a monoclonal antibody that specifically binds fPLP; and (b) detecting the binding of the fPLP in the sample to the antibody.

In another embodiment of the invention, the method further comprises contacting the sample with a first monoclonal antibody and a second antibody to form a complex, wherein both the first monoclonal antibody and the second antibody bind specifically to fPLP. The presence or amount of the complex is indicative of the presence or amount of fPLP in the sample. In one preferred embodiment, either the first monoclonal antibody or the second antibody is labeled. In certain embodiments, the second antibody can be a polyclonal antibody or a second monoclonal antibody.

In yet another embodiment of the invention, the first monoclonal antibody and the second antibody is either labeled or immobilized on a solid substrate, and the method for determining the presence or amount of fPLP in a sample further comprises a step of removing any unbound material from the substrate. It is understood that the first monoclonal antibody and the second antibody can be added to the biological sample either simultaneously or sequentially.

In one aspect, the current invention provides a method for determining the presence or amount of feline pancreatic lipase polypeptide (fPLP) in a biological sample comprising the steps of (a) contacting the sample with a first monoclonal antibody and a second antibody to form a complex, wherein both the first monoclonal antibody and the second antibody bind specifically to fPLP; and (b) detecting the presence or amount of the complex, wherein the presence or amount of the complex is indicative of the presence or amount of fPLP. In yet another embodiment of the invention, between the first monoclonal antibody and the second antibody, one comprises a label and the other is immobilized on a solid substrate, and wherein the presence or amount of the complex is measured by the amount of the signal from the label bound to the substrate. In a further embodiment of the invention, the method further comprises a step of removing any unbound material from the solid substrate. In a further embodiment, the second antibody is a second monoclonal antibody.

In another embodiment of the invention, the method further comprises the use of a standard, and comprises steps of contacting the first monoclonal antibody and the second monoclonal antibody with a standard to form a complex, said standard comprising recombinant fPLP; and comparing the presence or amount of the complex formed by the first and second monoclonal antibodies and fPLP in the sample to the presence or amount of the complex formed by the first and second monoclonal antibodies and fPLP in the standard. The standard or calibrators as used herein comprises native or recombinant fPLP.

In one embodiment of the invention, at least one of the first monoclonal antibody and the second monoclonal antibody is selected from the group consisting of FPL 17A.1D.12 and FPL2 35B.4B.1. In another embodiment, the sensitivity of detection is at least 10 μg fPLP/L. In yet another embodiment of the invention, the sensitivity of detection is at least 1 μg fPLP/L. As mentioned above, the mAb designations of FPL 17A.1D.12 and FPL2 35B.4B.1 are used interchangeably with PTA-8506 and PTA-8507, respectively.

Accordingly, in one aspect, the invention provides methods for determining the presence or amount of feline pancreatic lipase in a biological sample comprising: (a) contacting the sample with a first monoclonal antibody that specifically binds feline pancreatic lipase; and (b) detecting the binding of the feline pancreatic lipase in the sample to the first monoclonal antibody, wherein the first monoclonal antibody is PTA-8506, PTA-8507, or a monoclonal antibody that competes with either PTA-8506 or PTA-8507 for binding to feline pancreatic lipase. In one embodiment, the first monoclonal antibody is directly or indirectly immobilized on a solid surface. In another embodiment, the detecting further comprises: contacting the solid phase with a second antibody specific for feline pancreatic lipase, wherein the second antibody is directly or indirectly conjugated to a label; and detecting the label bound to the solid phase, wherein the first monoclonal antibody and the second antibody do not compete for binding to the feline pancreatic lipase. In certain embodiments, the second antibody is a second monoclonal antibody. The second monoclonal antibody includes without limitation PTA-8506, PTA-8507, or a monoclonal antibody that competes with either PTA-8506 or PTA-8507 for binding to feline pancreatic lipase.

In another aspect, the invention provides methods for determining the presence or amount of feline pancreatic lipase in a biological sample comprising: (a) forming a mixture of the sample with a first monoclonal antibody that specifically binds feline pancreatic lipase, wherein the first monoclonal antibody is conjugated to a label; (b) allowing the feline pancreatic lipase in the sample and the first monoclonal antibody to form a complex; (c) contacting the mixture with a second monoclonal antibody that binds to feline pancreatic lipase wherein the second monoclonal antibody is immobilized on a solid phase; and (d) detecting the presence or amount of the label on the solid phase, wherein at least one of the first monoclonal antibody and the second monoclonal antibody is PTA-8506, PTA-8507, or a monoclonal antibody that competes with either PTA-8506 or PTA-8507 for binding to feline pancreatic lipase, and wherein the first monoclonal antibody and the second monoclonal antibody do not compete for binding to the feline pancreatic lipase.

In a further aspect, the invention provides methods for determining the presence or amount of feline pancreatic lipase in a biological sample comprising: (a) forming a mixture of the sample with a first monoclonal antibody that specifically binds feline pancreatic lipase, wherein the first monoclonal antibody is conjugated to a first label; (b) allowing the feline pancreatic lipase in the sample and the first monoclonal antibody to form a complex; (c) contacting the mixture with a second monoclonal antibody that specifically binds to feline pancreatic lipase, wherein the second monoclonal antibody is conjugated to a second label; and (d) detecting the association of the labels, thereby detecting the presence of feline pancreatic lipase in the sample, wherein at least one of the first monoclonal antibody and the second monoclonal antibody is PTA-8506, PTA-8507, or a monoclonal antibody that competes with either PTA-8506 or PTA-8507 for binding to feline pancreatic lipase, and wherein the first monoclonal antibody and the second monoclonal antibody do not compete for binding to the feline pancreatic lipase. In certain embodiments, the label on the second monoclonal is a solid phase.

In another embodiment of the invention, the first and second antibodies are added sequentially. In one embodiment, the sample or standard is first contacted with the first monoclonal antibody to form a first complex, and then the first complex is contacted with the second monoclonal antibody to form a second complex.

In yet another embodiment, the sample or standard is first contacted with the second monoclonal antibody to form a first complex, wherein the first complex is contacted with the first monoclonal antibody to form a second complex.

"Binding specificity" or "specific binding" refers to the substantial recognition of a first molecule for a second molecule, for example a polypeptide and a polyclonal or monoclonal antibody, or an antibody fragment (e.g. a Fv, single chain Fv, Fab', or F(ab')$_2$ fragment specific for the polypeptide.

A "specific binding pair" (sbp) is a set of two different molecules, where one molecule has an area on its surface or in a cavity that specifically binds to, and is therefore complementary to, an area on the other molecule. "Specific binding partner" refers to one of these two complementarily binding molecules. "Specific binding reagent" comprises at least one of these complementarily binding molecules. "Specific binding pair" may refer to a ligand and a receptor, for example. In another example, the specific binding pair might refer to an immunological pair, for example an antigen and antibody.

"Substantial binding" or "substantially bind" refer to an amount of specific binding or recognizing between molecules in an assay mixture under particular assay conditions. In its broadest aspect, substantial binding relates to the difference between a first molecule's incapability of binding or recognizing a second molecule, and the first molecules capability of binding or recognizing a third molecule, such that the difference is sufficient to allow a meaningful assay to be conducted distinguishing specific binding under a particular set of assay conditions, which includes the relative concentrations of the molecules, and the time and temperature of an incubation. In another aspect, one molecule is substantially incapable of binding or recognizing another molecule in a cross-reactivity sense where the first molecule exhibits a reactivity for a second molecule that is less than 25%, preferably less than 10%, more preferably less than 5% of the reactivity exhibited toward a third molecule under a particular set of assay conditions, which includes the relative concentration and incubation of the molecules. Specific binding can be tested using a number of widely known methods, e.g., an immunohistochemical assay, an enzyme-linked immunosorbent assay (ELISA), a radioimmunoassay (RIA), or a western blot assay.

A "biological sample" refers to a sample from an animal subject including whole blood, serum, plasma, tissue, abdominal fluid (ascites), urine or other sample known or suspected to contain feline pancreatic lipase.

As used herein, an antibody "comprising a label" refers to an antibody that is directly or indirectly labeled. A "label" or a signal generating molecule is any molecule that is bound (via covalent or non-covalent means, alone or encapsulated) to another molecule or solid support and that is chosen for specific characteristics that allow detection of the labeled molecule. Generally, labels are comprised of, but are not limited to, the following types: particulate metal and metal-derivatives, radioisotopes, catalytic or enzyme-based reactants, chromogenic substrates and chromophores, fluorescent and chemiluminescent molecules, and phosphors. The utilization of a label produces a signal that may be detected by means such as detection of electromagnetic radiation or direct visualization, and that can optionally be measured. Examples of indirect labeling include, but not limited to, addition of a molecule that binds specifically to the first antibody, wherein the molecule is able to produce a signal on its own or is conjugated to another signal generating molecule. For instance, the indirect labeling can be achieved by the interaction of biotin and streptavidin, wherein a biotinylated first antibody is contacted with the streptavidin-conjugated signal generating molecule. The interaction of biotin and streptavidin confers the labeling to the first antibody. Alternatively, the first antibody can be labeled by a third antibody that specifically binds to the first antibody, wherein the third antibody is conjugated to a label, such as a HRPO enzyme conjugate. It is within the knowledge and ability of one of ordinary skill in the art to modify the invention in this aspect with regard to the make and use of a labeled first antibody.

The label employed in the current invention could be, but is not limited to: alkaline phosphatase; glucose-6-phosphate dehydrogenase ("G6PDH"); horse radish peroxidase (HRP); chemiluminescers such as isoluminol, fluorescers such as fluorescein and rhodamine compounds; ribozymes; and dyes.

The label can directly produce a signal, and therefore additional components are not required to produce a signal. Alternatively, a label may need additional components, such as substrates or co-enzymes, in order to produce a signal. The suitability and use of such labels useful for producing a signal are discussed in U.S. Pat. No. 6,489,309, and U.S. Pat. No. 5,185,243, which are incorporated by reference herein in their entirety. For example, a label may be conjugated to the specific binding partner in a non-covalent fashion. Alternatively, the label may be conjugated to the specific binding partner covalently. U.S. Pat. No. 3,817,837, and U.S. Pat. No. 3,996,345, which are incorporated by reference herein in their entirety, describe in detail example of various ways that a label may be non-covalently or covalently conjugated to the specific binding partner.

The antibody immobilized on a solid substrate is also referred to as a capture antibody. The antibody in solution that is directly or indirectly labeled is also referred to as a detection antibody. In one embodiment of the invention, the capture antibody and the detection antibody are selected from the group consisting of FPL 17A.1D.12 and FPL2 35B.4B.1. In one embodiment, FPL 17A.1D.12 is the capture antibody and FPL2 35B.4B.1 is the detection antibody. In yet another embodiment, FPL2 35B.4B.1 is the capture antibody, and FPL 17A.1D.12 is the detection antibody.

"Solid phase", "substrate" or "solid substrate" means a porous or non-porous water insoluble material. Such materials include a support or a surface such as the wall of a reaction vessel. The support can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc., synthetic or modified naturally occurring polymers, such as nitrocellulose, cellulose acetate, poly (vinyl chloride), polyacrylamide, cross linked dextran, agarose, polyacrylate, polyethylene, polypropylene, poly(4-methylbutene), polystyrene, polymethacrylate, poly(ethylene terephthalate), nylon, poly(vinyl butyrate), etc.; either used by themselves or in conjunction with other materials; glass available as Bioglass, ceramics, metals, and the like. Natural or synthetic assemblies such as liposomes, phospholipid vesicles, and cells can also be employed.

Binding of sbp members to a support or surface may be accomplished by well-known techniques, commonly available in the literature. See, for example, "Immobilized Enzymes," Ichiro Chibata, Halsted Press, New York (1978) and Cuatrecasas, J. Biol. Chem., 245:3059 (1970). The surface can have any one of a number of shapes, such as strip, rod, particle, including bead, and the like. In one aspect, the polypeptides of the invention include a N-terminal cysteine residue to assist in binding the polypeptides to the solid phase or the substrate.

The method of the invention can be optimized in many ways and one of skill in the art could simultaneously adjust the sample dilutions, reagent concentrations, incubation temperatures and times used in the method to accomplish detection of feline pancreatic lipase.

To be useful in the detection methods of the present invention, the polypeptides are obtained in a substantially pure form, that is, typically from about 50% w/w to more purity, substantially free of interfering proteins and contaminants. Preferably, the polypeptides are isolated or synthesized in a purity of at least 80% w/w, and more preferably, in at least about 95% w/w purity. Using conventional protein purification techniques, homogeneous polypeptide compositions of at least about 99% w/w purity can be obtained. For example, the proteins may be purified by use of the antibodies described hereinafter using the immunoabsorbant affinity columns described hereinabove.

The method of the invention may be accomplished using immunoassay techniques well known to those of skill in the art, including, but not limited to, using microplates and lateral flow devices. In one embodiment, an antibody specific for feline pancreatic lipase protein is immobilized on a solid support at a distinct location. Following addition of the sample, detection of protein-antibody complexes on the solid support can be by any means known in the art. For example, U.S. Pat. No. 5,726,010, which is incorporated herein by reference in its entirety, describes an example of a lateral flow device, the SNAP immunoassay device (IDEXX Laboratories), useful in the present invention. In another aspect, the solid support is a well of a microtiter plate.

The device of the invention may be made by immobilizing one or more analyte capture reagents, e.g., antibodies to feline pancreatic lipase, onto a device or solid support so that the analyte capture reagent will not be washed away by the sample, diluent and/or wash procedures. One or more analyte capture reagents can be attached to a surface by physical adsorption (i.e., without the use of chemical linkers) or by chemical binding (i.e., with the use of chemical linkers). Chemical binding can generate stronger attachment of specific binding substances on a surface and provide defined orientation and conformation of the surface-bound molecules. The analyte capture reagents include, but are not limited to, a polyclonal or monoclonal antibody to feline pancreatic lipase protein, or substrate to the feline pancreatic lipase protein or a non-competitive or competitive inhibitor of the enzyme that captures the enzyme.

In another aspect, the invention includes one or more labeled specific binding reagents, e.g., antibodies, which can be mixed with a test sample prior to application to a device of the invention. In this case it is not necessary to have labeled specific binding reagents deposited and dried on a specific binding reagent pad in the device. A labeled specific binding reagent, whether added to a test sample or pre-deposited on the device, can be for example, a labeled feline pancreatic lipase monoclonal or polyclonal antibody. The specific binding reagent can be labeled with, for example, a chemical moiety that is coupled to the specific binding reagent to enable detection of the specific binding reagent. The chemical moiety may be selected from the group, including but not limited to, a radiolabel, an enzyme such as horseradish peroxidase or alkaline phosphatase, streptavidin, biotin, an epitope recognized by an antibody, and equivalents thereof.

In one embodiment of the invention, the capture reagent and the labeled specific binding reagent are antibodies that specifically bind feline pancreatic lipase. When the analyte capture reagent and the labeled specific binding reagent are antibodies that specifically bind feline pancreatic lipase, the antibodies are different. In one aspect, the antibodies are chosen from FPL 17A.1D.12 and FPL2 35B.4B.1.

The detection method may include the use of a standard or calibrator such as a purified native or, preferably, recombinant feline pancreatic lipase polypeptide. The standard can be mixed with the monoclonal antibody or antibodies in the same manner as the sample. The amount of binding between the monoclonal antibody or antibodies and the standard can be compared to the amount of binding of the antibodies to the protein in the sample. Accordingly, because the amount of feline pancreatic lipase in the standard is known, the amount of protein in the sample can be determined.

The reagents, device, and method of the invention can be applied for the determination or diagnosis of pancreatic lipase related diseases in an animal subject. In one aspect, the invention provides a method for determining whether a feline subject has pancreatitis. The method of the invention comprises steps of (a) obtaining a sample from the feline subject; (b) contacting the sample with a first monoclonal antibody specific for feline pancreatic lipase polypeptide (fPLP) and a second antibody specific for fPLP to form a complex, (c) providing a standard, said standard comprising recombinant fPLP; (d) contacting the standard with the first monoclonal antibody and the second monoclonal antibody to form a complex; and (e) determining whether the feline subject has pancreatitis by comparing the presence or amount of the complex formed by the first and second monoclonal antibodies with fPLP in the sample to the presence or amount of the complex formed by the first and second monoclonal antibodies with fPLP in the standard, wherein the presence or amount of the complex is measured by the amount of the label bound to the substrate.

In one embodiment of the invention, one of the first monoclonal antibody and the second antibody comprises a label and the other is immobilized on a solid substrate. In another embodiment of the invention, the second antibody is a monoclonal antibody.

In yet another embodiment of the invention, the first monoclonal antibody comprises a label and the second monoclonal antibody is immobilized on a solid substrate. In yet another embodiment of the invention, the method further comprises contacting the first and second monoclonal antibody with a standard that comprises fPLP. The sample or standard could be contacted with the first and the second monoclonal antibodies simultaneously or sequentially.

Any or all of the above embodiments can be provided as a kit. In one particular example, such a kit would include a device complete with specific binding reagents (e.g., a non-immobilized labeled specific binding reagent and an immobilized analyte capture reagent) and wash reagent, as well as detector reagent and positive and negative control reagents, if desired or appropriate. In addition, other additives can be included, such as stabilizers, buffers, and the like. The relative amounts of the various reagents can be varied, to provide for concentrations in solution of the reagents that substantially optimize the sensitivity of the assay. Particularly, the reagents can be provided as dry powders, usually lyophilized, which on dissolution will provide for a reagent solution having the appropriate concentrations for combining with a sample.

The device may also include a liquid reagent that transports unbound material (e.g., unreacted fluid sample and unbound specific binding reagents) away from the reaction zone (solid phase). A liquid reagent can be a wash reagent and serve only to remove unbound material from the reaction zone, or it can include a detector reagent and serve to both remove unbound material and facilitate analyte detection. For example, in the case of a specific binding reagent conjugated to an enzyme, the detector reagent includes a substrate that produces a detectable signal upon reaction with the enzyme-antibody conjugate at the reactive zone. In the case of a labeled specific binding reagent conjugated to a radioactive, fluorescent, or light-absorbing molecule, the detector reagent acts merely as a wash solution facilitating detection of complex formation at the reactive zone by washing away unbound labeled reagent.

Two or more liquid reagents can be present in a device, for example, a device can comprise a liquid reagent that acts as a wash reagent and a liquid reagent that acts as a detector reagent and facilitates analyte detection.

A liquid reagent can further include a limited quantity of an "inhibitor", i.e., a substance that blocks the development of the detectable end product. A limited quantity is an amount of inhibitor sufficient to block end product development until most or all excess, unbound material is transported away from the second region, at which time detectable end product is produced.

In another aspect, the invention is directed to a kit for detecting feline pancreatic lipase. For example the kit can include the device described above, along with the antibodies described herein. One or more of the peptides of the invention can be included as a calibrator and control. Such a kit can be supplied to detect a single protein or epitope or can be configured to detect one of a multitude of epitopes, such as in an antibody detection array. In one aspect, the kit includes a solid phase or substrate, such as a microtiter plate or lateral flow device, having an immobilized antibody specific for feline pancreatic lipase, a reagent comprising a second labeled antibody specific for feline pancreatic lipase, and reagents for use in detecting the label. The kit also includes the appropriate packaging and instructions.

Other features and advantages of the invention will be apparent from the following Examples. The following are provided for exemplification purposes only and are not intended to limit the scope of the invention described above. All references cited in this disclosure are incorporated herein by reference.

EXAMPLE 1

Cloning and Characterization of the Feline Pancreatic Lipase (fPL) Gene from Pancreatic Tissue Based on the published N-terminal amino acid sequence of feline pancreatic lipase (Steiner et al. U.S. Pat. No. 6,855,506) (SEQ ID NO:1) and sequence similarities among pancreatic lipase of other species, a series of degenerate primers were designed and used for 5' RACE (Rapid Amplification of cDNA Ends) and 3' RACE to the sequence of feline pancreatic lipase gene from pancreatic RNA. The 3' RACE primers used were RACE 5, SEQ ID NO:4, and UPM (Universal Primer Mix), SEQ ID NO:5 and SEQ ID NO:6. The 5' RACE primers used were KC616, SEQ ID NO:7 and UPM, SEQ ID NO:5 and SEQ ID NO:6. The primers KC616 and RACE 5 target specific regions of the pancreatic lipase sequence which differentiate it from other members of the pancreatic lipase family, such as pancreatic lipase related proteins.

Total RNA was purified from homogenized feline pancreas using TRIZOL reagent (Invitrogen, Cat# 15596-026) according to manufacturer's instructions. 5' RACE and 3' RACE are techniques will known to those schooled in the art. These methods are facilitated by commercially available kits such as the SMART™ RACE cDNA Amplification Kit (Clontech, Mountain View, Calif. 94043). The specific primer for 3' RACE, RACE 5 (SEQ ID NO.4), was designed using alignments of pancreatic lipase genes, including canine pancreatic lipase (See U.S. Patent Application Publication No. 2005/0233368, which is incorporated herein by reference in its entirety). The PCR products from these experiments were TOPO Cloned into pCRII (Invitrogen Corporation, Carlsbad, Calif. 92008) and sequenced. For 5' RACE, the specific primer for amplification of the 5' portion of the gene was Kc616 (SEQ ID NO:7), which was designed using the sequenced portion of the feline pancreatic lipase gene obtained through 3' RACE. This PCR product was TOPO Cloned into pCRII (Invitrogen) and sequenced. The fPL cDNA sequence is shown in FIG. 3 and designated as SEQ ID NO:2, and the deduced amino acid sequence is shown in FIG. 4, SEQ ID NO:3.

A full length gene PCR product was generated using pancreatic cDNA as a template with primer sets Kc626/Kc630, SEQ ID NO:8 and SEQ ID NO:9. A flow chart and schematic diagram of the cloning of full length fPL cDNA is shown in FIG. 2. The full length fpL PCR product was verified by agarose gel electrophoresis. This DNA was used as a template for PCR using PCR primers "fpl-4_xho1Stop" (SEQ ID NO:10) and "fpl-3_hindIII" (SEQ ID NO:11). The full length PCR product was verified and isolated using agarose gel electrophoreis, digested with the restriction enzymes XhoI and HinDIII, and subsequently cloned into an appropriately prepared pBAC1 vector (Novagen, San Diego, Calif. 92121). The sequence of this clone was verified using the Sanger dideoxy chain termination method. (See, for example, Maniatis et al., MOLECULAR CLONING: A LABORATORY MANUAL, 3rd Ed., 2001, Cold Spring Harbor, N.Y. and Berger, which is incorporated herein by reference.)

EXAMPLE 2

Expression and Purification of Feline Pancreatic Lipase

Expression and purification of fPLP from baculoviral culture supernatant essentially follows the protocol of Thirstrup et al. (FEBS Lett. 1993. 327:79-84). Briefly, pBAC-1 XhoI/HindIII clone of fPLP was used in co-transfection of *Spodoptera frugiperda* (SF9) insect cells with wild-type *Autographa Californica* nuclear polyhedrosis virus (AcNPV) DNA. A stable, recombinant baculovirus was developed using methods well known to those schooled in the art (Maniatis et al., MOLECULAR CLONING: A LABORATORY MANUAL, 3rd Ed., 2001, Cold Spring Harbor, N.Y.). An fPLP baculovirus stock was used to infect SF9 cultures at a 1 liter scale. Cell culture was harvested on day 3, clarified and frozen at −70° C. One liter of frozen, clarified SF9 cell culture supernatant was removed from the −70° C. freezer and allowed to thaw overnight at 4° C. This material was dialyzed against 10 liters of 50 mM MES pH6.5, 5 mM NaCl (referred to as Buffer A) at 4° C. using dialysis tubing with an 8 KDa MW cutoff (Spectra/Por 7, Spectrum Laboratories Inc., Rancho Dominguez, Calif. 90220). Sodium azide was added to 0.02% to inhibit bacterial growth. The dialysis buffer was changed 2 more times during the course of dialysis, for a total dialysis time of 24 hours. The dialysate was filtered using a 0.45 um HV Durapore Membrane Filter Device (Millipore, Billerica, Mass. 01821) and loaded onto a 10 ml SP column that was created by joining two 5-ml SP HiTrap columns (GE Amersham Biosciences, Piscataway, N.J. 08855) followed by pre-equilibration with Buffer A. All chromatography steps were done at room temperature (approximately 20° C. to 22° C.). The loaded sample was washed with 10 column volumes of Buffer A, followed by a linear 10 column volumes gradient of Buffer B (50 mM MES, pH6.5, 1 M NaCl) at a flow rate of 2 ml/min. Five ml fractions were collected and analyzed for lipase activity as well as protein content using SDS-PAGE followed by staining with Coomassie Brilliant Blue. Fractions were pooled and dialyzed overnight against PBS (phosphate buffered saline). The dialysate was sterile filtered using a 0.45 um filter, aliquoted and frozen at −70° C. TABLE 2 outlines the major steps of the described protocol. Protein concentration was determined spectrophotometrically at OD280 with a molar extinction coefficient of 1.1525 for fPLP. On average, the described method enables an approximate 2,500 fold purification of fPLP, producing approximately 3.5 mgs of fPLP from 1 L of baculovirus culture supernatant.

TABLE 2

| Name | Units Activity per ml | Volume (L) | Total Lipase Activity | % Starting Material | Protein Concentration mgs/ml | Mgs Total Protein | Specific Activity | Fold Purification |
|---|---|---|---|---|---|---|---|---|
| Clarified Sup. | 1582 | 1.1 | 1794.1 | 100.0 | 13.545 | 14899.5 | 0.12 | 1 |
| Dialysate | 1668 | 1.15 | 1934.3 | 107.8 | 13.6138 | 15655.87 | 0.12 | 1 |
| Filtered Dial. | 1542 | 1.15 | 1772.15 | 98.8 | 1.7028 | 1958.22 | 0.90 | 8 |
| Pooled Fractions | 218750 | 0.005 | 1282.5 | 71.5 | 1.204 | 6.02 | 213.04 | 1775 |
| Dialyzed Fractions | 211400 | 0.0045 | 1119.975 | 62.4 | 0.8342 | 3.7539 | 298.35 | 2486 |
| Filtered Fractions | 195650 | 0.0045 | 1101.975 | 61.4 | 0.774 | 3.483 | 316.39 | 2637 |

The purity of baculoviral expressed fPL protein sample purified based on the purification scheme described above was examined by gel electrophoresis followed by Coomassie blue staining of the gel. As shown in FIG. 5, in one representative experiment, after sequential purification, the purity of fPLP (indicated by arrow) after the final filtration step is estimated to be 60%.

EXAMPLE 3

Production of Monoclonal Antibody Specific for Feline Pancreatic Lipase Protein

Native fPLP protein isolated from cat pancreas was the immunogen used for the development of fPLP specific monoclonal antibodies (purification see U.S. Pat. No. 6,855,506, which is incorporated herein by reference). Two different immunization regimes were used to immunize mice—both of which generated mAbs specific for fPLP. The first regime started with an initial injection at day 0 (IP, Freunds complete adjuvant), with boosts on days 14 (IP, incomplete Freunds adnuvant), 30 (SC, ImmunEasy Adjuvant, Qiagen), 31 (IP, no adjuvant) followed by fusion on day 34. Concentration of antigen for each boost was 100 µg, 50 µg, 10 µg, 100 µg respectively. The second regime started with an initial injection at day 0 (IP, Freunds Complete Adjuvant), followed by boosts on days 14 (Freund's incomplete adjuvant), 30 (SC, ImmunEasy Adjuvant, Qiagen), 31 (IP, no adjuvant), 55 (SC, ImmunEasy Adjuvant), 78 (Titermax Gold adjuvant, Sigma), 119 (SC, Ribi adjuvant System, Sigma), 134 (SC, Ribi adjuvant system), 149 (SC, Ribi adjuvant system), 162 (SC, Titermax Gold Adjuvant), 175 (IP, no adjuvant)., and 176 (IP, no adjuvant) with fusion on day 179. Concentration of the immunogen was 100 µg, 50 µg, 10 µg, 100 µg, 10 µg, 10 µg, 10 µg, 10 µg, 10 µg, 10 µg, 100 µg, and 25 µg, respectively,

EXAMPLE 4

Characterization of Feline Pancreatic Lipase Monoclonal Antibody

Next, the dose responsiveness of the feline pancreatic lipase monoclonal antibody is determined. The amount of 10 µg/ml of capture antibody feline PLP monoclonal Ab 17A.1D.12 is coated on each well across the entire microtiter plate at 4° C. for twelve hours. The plate was then washed and blocked with 1% BSA (four hours at 20° C.) before receiving a final overcoat of 2.5% sucrose (six hours at 4° C.). The HRPO-conjugated detection fPLP monoclonal antibody FLP2 35 B.4B.1 was mixed with the calibrator native or recombinant fPL protein and the mixture was incubated on the plate for one hour at 25° C. The HRPO-conjugated secondary monoclonal antibody was used at a dilution of 1:2500 from a stock solution of 0.65 mg/mL HRPO-conjugated FLP2 35 B.4B.1.

Figure 6:
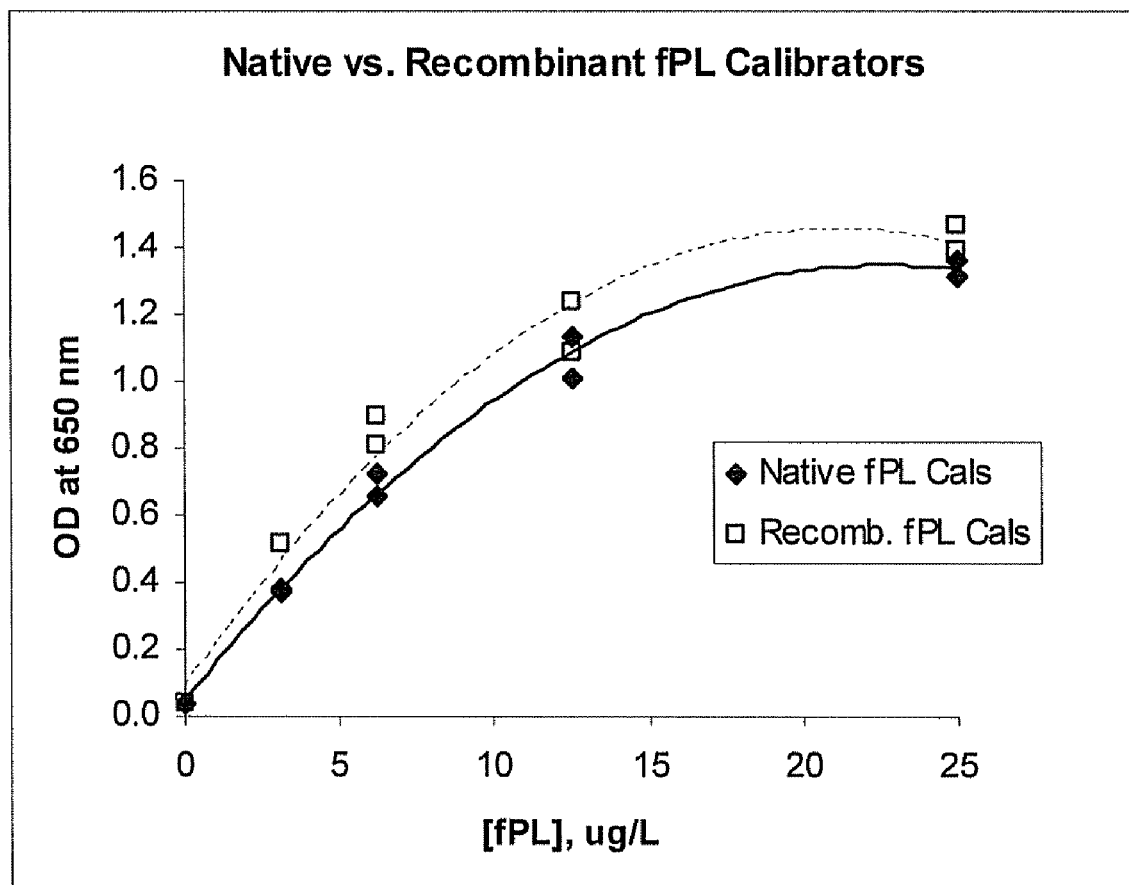
FIG. 6 shows the results of an ELISA assay determining dose responsiveness of the feline pancreatic lipase monoclonal antibodies FPL 17A.1D.12 and FPL2 35B.4B.1 to equivalent concentrations of native fPLP extracted from feline pancreases, and recombinant fPLP. In this experiment, FPL 17A.1D.12 was used as capture antibody, and FPL2 35B.4B.1 was used as detection antibody.

At the end of the incubation time, the plate is washed to remove any unbound components. TMB substrate (3,3',5,5'-tetramethylbenzidene) is added to the wells, and the plate is incubated for 5 minutes at room temperature. The color reaction is stopped with the addition of 1% SDS solution, and absorbance values are read at 650 nm using a microtiter plate reader. Results of the ELISA assays using native fPLP calibrators and recombinant fPLP calibrators are shown in FIG. 6. The calibration curve as shown in FIG. 6 is generated by capturing known concentration of native or recombinant fPLP antigen onto the plate. The HRPO-antibody conjugate is prepared using HRPO-SMCC and a disulfide reduced form of the antibody. Stimmel et al 2000 J. Biol. Chem. 275(39):30445-50; Imagawa et al 1982 J. Appl. Biochem. 4, 41-57. The sensitivity of the monoclonal antibody reaches at least µg/L range for both the native fPLP protein and the recombinant fPLP protein. The ELISA experiment using FLP2 35 B.4B.1 as capture antibody and FLP 17A.1D.12 as detection antibody yielded similar results.

EXAMPLE 5

Figure 7:
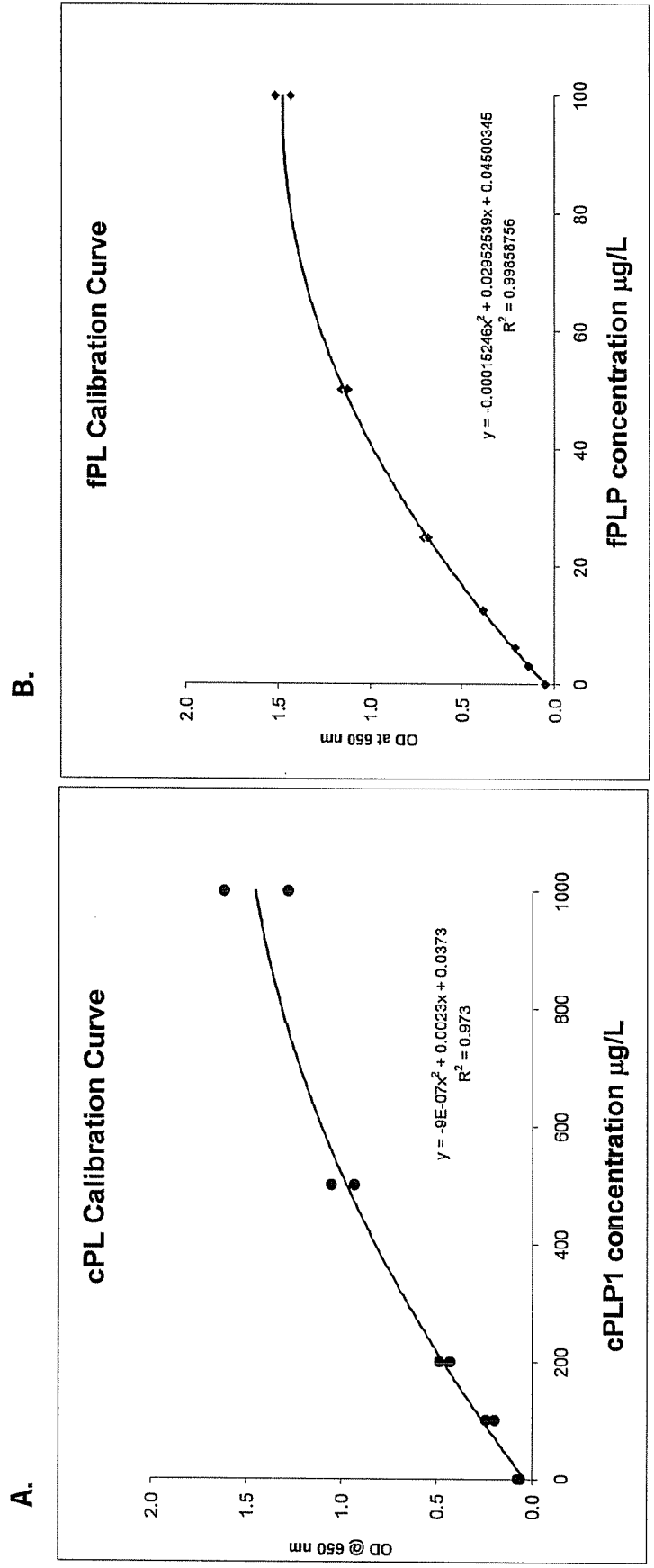
FIG. 7 shows a diagram depicting the comparison of detection sensitivity of feline pancreatic lipase monoclonal antibody of the invention (Panel B) with that of the canine pancreatic lipase monoclonal antibody (Panel A). Under equivalent ELISA assay conditions, the feline monoclonal antibody generates equivalent signal at an antigen concentration that is ten times lower than the concentration of canine pancreatic lipase protein. In this experiment, FPL 17A.1 D.12 was used as capture antibody, and FPL2 35B.4B.1 was used as detection antibody.

Comparison of Feline Pancreatic Lipase Monoclonal Antibody with Canine Pancreatic Lipase Monoclonal Antibody The detection sensitivity of fPLP monoclonal antibody for recombinant fPLP is compared with that of the canine pancreatic lipase specific monoclonal antibody for recombinant canine pancreatic lipase polypeptide (cPLP1). The ELISA conditions for detecting fPLP are as described above. For cPLP ELISA, cPLP monoclonal antibody 7E11 was used as the capture antibody, and HRPO-conjugated cPLP monoclonal antibody 4G11 was used as the detection antibody. See U.S. patent application Ser. No. 11/107,086, filed Apr. 15, 2005 and published as U.S. Patent Application No. 2005-0233368, which is incorporated herein by reference in its entirety. In both the CPLP and FPLP ELISAs, the plates were coated with 5.0 µg/mL (0.100 mL per well over entire plate) of the respective capture antibody, FPL 17A.1D.12 for FPLP and CPL 7 µl 1 for CPLP. For FPLP, detection antibody was used at a 1:5000 dilution from a stock solution of 1.24 mg/mL HRPO-conjugated FLP2 35 B.4B.1. For CPLP, detection antibody was used at a 1:3000 dilution from a stock of 0.71 mg/mL HRPO-conjugated 4G11. As shown in FIG. 7, fPLP antibody generates equivalent signals at an fPLP concentration that is ten times lower than the concentration of cPLP1.

Thus, the fPLP monoclonal antibody is at least ten times more sensitive than the cPLP1 monoclonal antibody.

EXAMPLE 6

Figure 8:
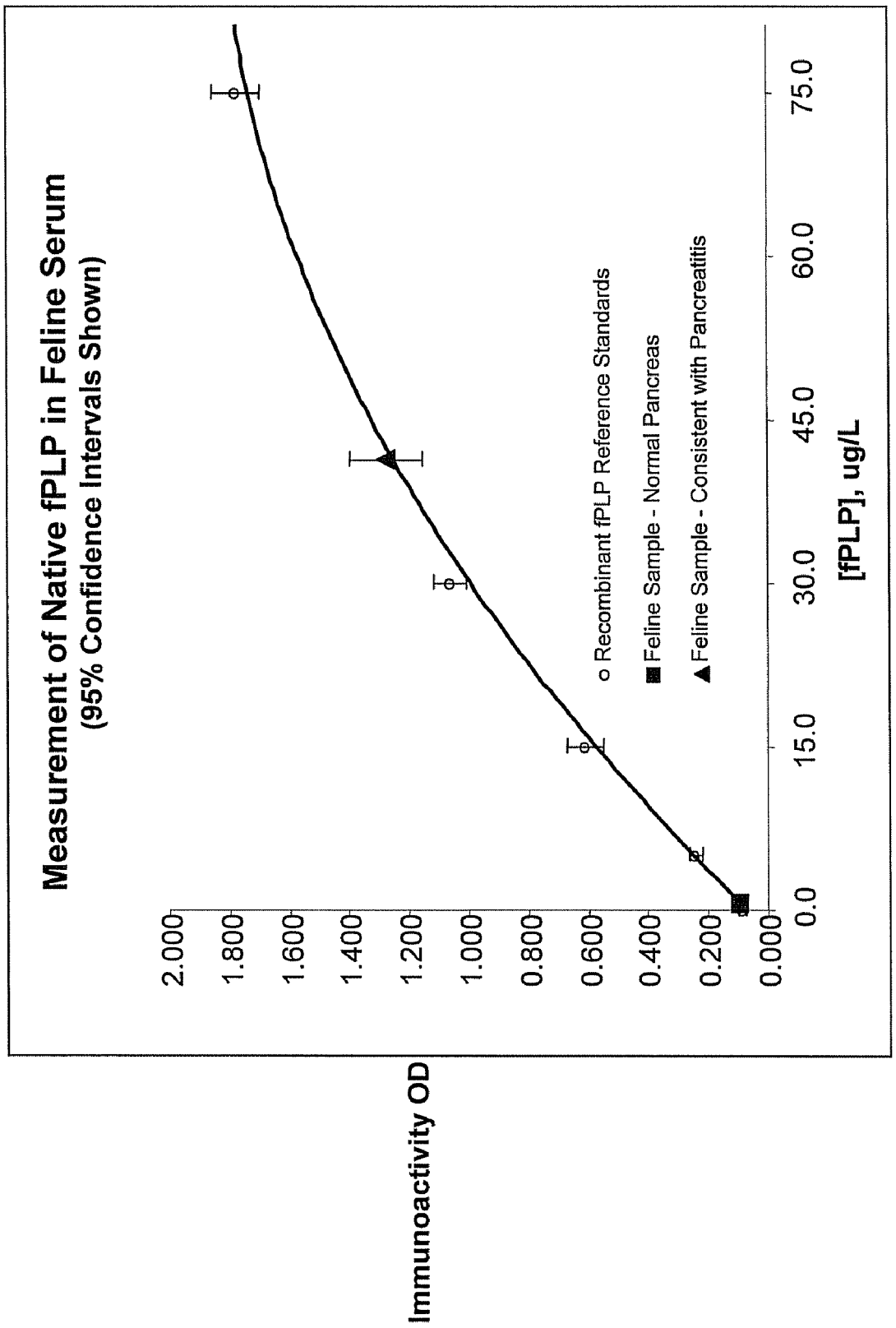
FIG. 8 shows a diagram depicting dose response of native fPLP in two feline serum samples—one from a cat with a normal pancreas (■) and one from a cat with an inflamed pancreas (▲)—in comparison with recombinant fPLP reference standards. Independent confirmation of these samples was performed by assaying for feline pancreatic lipase immunoreactivity (fPLI). The normal sample yields no significant response while the sample from the cat with pancreatic inflammation produces a significant elevated response. In this experiment, FPL 17A.1D.12 was used as capture antibody, and FPL2 35B.4B.1 was used as detection antibody.

Detecting and Measuring Native Feline Pancreatic Lipase Protein in Feline Samples FIG. 8 shows the dose response of native fPLP in two feline serum samples—one from a cat with a normal pancreas (■) and the other from a cat with an inflamed pancreas (▲)—in comparison with recombinant fPLP reference standards.

Independent confirmation of these samples was performed by assaying for feline pancreatic lipase immunoreactivity using fPLP polyclonal antibody as described in U.S. Pat. No. 6,855,506. The sample from normal cat yields no significant response, while the sample from the cat with pancreatic inflammation produces a significant elevated response to fPLP monoclonal antibody. In this experiment, FPL 17A.1D.12 was used as capture antibody, and FPL2 35B.4B.1 was used as detection antibody. The result shows that the high levels of fPLP in a feline sample detected by using fPLP monoclonal antibody described herein can be relied upon as an indicator for pancreatitis in a feline subject.

What is claimed is:

1. A method for determining the presence or amount of feline pancreatic lipase polypeptide (fPLP) in a biological sample comprising:
   (a) contacting the sample with a monoclonal antibody that specifically binds fPLP; and
   (b) detecting the binding of the fPLP in the sample to the antibody;
   wherein the monoclonal antibody is the monoclonal antibody produced by hybridoma cell line designated under the ATCC deposit No. PTA-8506 or PTA 8507 or a monoclonal antibody that competes for the epitope that binds the monoclonal antibody produced by hybridoma cell line PTA-8506 or PTA 8507 on feline pancreatic lipase.

2. The method of claim 1, further comprising (i) contacting a standard with the monoclonal antibody, said standard comprising recombinant fPLP, (ii) detecting the binding of the fPLP in the standard to the monoclonal antibody, and (iii) comparing the amount of binding of the monoclonal antibody to the fPLP in the sample to the amount of binding of the monoclonal antibody to the fPLP in the standard.

3. The method of claim 2, wherein the monoclonal antibody comprises a label, and wherein the amount of binding of the monoclonal antibody to fPLP is measured by the amount of the signal from the label.

4. The method of claim 1, wherein the monoclonal antibody is immobilized on a substrate.

5. The method of claim 4, wherein the monoclonal antibody is a first monoclonal antibody, said method further comprising contacting the sample or the standard with a second antibody specific for fPLP, said second antibody comprising a label, wherein the amount of binding of the first monoclonal antibody to the fPLP in the sample or to the fPLP in the standard is measured by the amount of signal from the label bound to the second antibody.

6. The method of claim 5, wherein the second antibody is a second monoclonal antibody specific for fPLP.

7. The method of claim 5, wherein the second antibody is a monoclonal antibody produced by hybridoma cell line designated under the American Type Culture Collection (ATCC) Patent Deposit No. PTA-8506 or PTA-8507 or a monoclonal antibody that competes for the epitope that binds the monoclonal antibody produced by hybridoma cell line PTA-8506 or PTA 8507 on feline pancreatic lipase, wherein the first and second monoclonal antibodies do not compete for the same epitope.

8. A method for determining the presence or amount of feline pancreatic lipase polypeptide (fPLP) in a biological sample comprising:
   (a) contacting the sample with a first monoclonal antibody and a second antibody to form a complex, wherein both the first monoclonal antibody and the second antibody bind specifically to fPLP; and
   (b) detecting the presence or amount of the complex,
   wherein the presence or amount of the complex is indicative of the presence or amount of fPLP, and
   wherein the first monoclonal antibody is a monoclonal antibody produced by hybridoma cell line designated under the ATCC deposit No. PTA-8506 or PTA-8507, or a monoclonal antibody that competes for the epitope that binds the monoclonal antibody produced by hybridoma cell line PTA-8506 or PTA 8507 on feline pancreatic lipase.

9. The method of claim 8, wherein the second antibody is a second monoclonal antibody.

10. The method of claim 8, wherein the first monoclonal antibody comprises a label and the second monoclonal antibody is immobilized on a solid substrate, and wherein the presence or amount of the complex is measured by the amount of the signal from the label bound to the substrate.

11. The method of claim 10, further comprising a step of removing any unbound material from the solid substrate.

12. The method of claim 11, wherein the first monoclonal antibody is directly labeled.

13. The method of claim 11, wherein the first monoclonal antibody is indirectly labeled, the method further comprising a step of contacting the complex with a labeled molecule that specifically binds to the first monoclonal antibody.

14. The method of claim 9, further comprising contacting the first monoclonal antibody and the second monoclonal antibody with a standard to form a complex, said standard comprising recombinant fPLP; and comparing the presence or amount of the complex formed by the first and second monoclonal antibodies and fPLP in the sample to the presence or amount of the complex formed by the first and second monoclonal antibodies and fPLP in the standard.

15. The method of claim 9, wherein the second monoclonal antibody is a monoclonal antibody produced by hybridoma cell line designated under the ATCC deposit No. PTA-8506 or PTA-8507, or a monoclonal antibody that competes for the epitope that binds the monoclonal antibody produced by hybridoma cell line PTA-8506 or PTA 8507 on feline pancreatic lipase, wherein the first and the second monoclonal antibodies do not compete for the same epitope.

16. The method of claim 8, wherein the sensitivity of detection is at least 100 g fPLP/L.

17. The method of claim 16, wherein the sensitivity of detection is at least 10 g fPLP/L.

18. The method of claim 8, wherein the sample is a whole blood sample, a serum sample, a plasma sample, an abdominal fluid sample or a urine sample.

19. The method of claim 14, wherein the sample is derived from a feline subject, and the comparison of the presence or amount of the complex formed by the first and second monoclonal antibodies to fPLP in the sample to the presence or amount of the complex formed by the first and second monoclonal antibodies and fPLP in the standard is indicative of a fPLP related condition in the feline subject.

20. The method of claim 19, wherein the condition is feline pancreatitis.

21. The method of claim 14, wherein the sample or standard is first contacted with the first monoclonal antibody to form a first complex, and wherein the first complex is contacted with the second monoclonal antibody to form a second complex.

22. The method of claim 14, wherein the sample or standard is first contacted with the second monoclonal antibody to form a first complex, and wherein the first complex is contacted with the first monoclonal antibody to form a second complex.

* * * * *

UNITED STATES PATENT AND TRADEMARK OFFICE
CERTIFICATE OF CORRECTION

PATENT NO. : 7,771,960 B2  Page 1 of 1
APPLICATION NO. : 12/252120
DATED : August 10, 2010
INVENTOR(S) : Andersen et al.

It is certified that error appears in the above-identified patent and that said Letters Patent is hereby corrected as shown below:

On the Title Page at item (75):

Please delete "Eugene Regis" and replace with "Eugene Regis Krah"

Signed and Sealed this

Fourteenth Day of September, 2010

David J. Kappos
*Director of the United States Patent and Trademark Office*

SEQUENCE LISTING

<160> NUMBER OF SEQ ID NOS: 16

<210> SEQ ID NO 1
<211> LENGTH: 15
<212> TYPE: PRT
<213> ORGANISM: Felis sp.
<220> FEATURE:
<221> NAME/KEY: MISC_FEATURE
<222> LOCATION: (4)..(4)
<223> OTHER INFORMATION: Xaa is unknown amino acid residue
<220> FEATURE:
<221> NAME/KEY: MISC_FEATURE
<222> LOCATION: (10)..(10)
<223> OTHER INFORMATION: Xaa is unknown amino acid residue

<400> SEQUENCE: 1

```
Lys Glu Ile Xaa Phe Pro Arg Leu Gly Xaa Phe Ser Asp Asp Ala
1               5                   10                  15
```

<210> SEQ ID NO 2
<211> LENGTH: 1398
<212> TYPE: DNA
<213> ORGANISM: Felis sp.
<220> FEATURE:
<221> NAME/KEY: CDS
<222> LOCATION: (1)..(1398)

<400> SEQUENCE: 2

```
atg ctg cta atc tgg aca cta tcg ctg ctg ctg gga gca gta gta gga      48
Met Leu Leu Ile Trp Thr Leu Ser Leu Leu Leu Gly Ala Val Val Gly
1               5                   10                  15 aaa gaa atc tgc ttc cca aga ctt ggc tgc ttt agc gat gat gcc cca      96
Lys Glu Ile Cys Phe Pro Arg Leu Gly Cys Phe Ser Asp Asp Ala Pro
                20                  25                  30 tgg gca gga att gcg caa aga ccc ctc aaa ata ttg ccc tgg cct cca     144
Trp Ala Gly Ile Ala Gln Arg Pro Leu Lys Ile Leu Pro Trp Pro Pro
            35                  40                  45 aaa gat gtc aat acc cgc ttc ctc ctg tac act aac gag aac ccg aat     192
Lys Asp Val Asn Thr Arg Phe Leu Leu Tyr Thr Asn Glu Asn Pro Asn
        50                  55                  60 aac ttt gaa gaa att att gca gat gaa tca act atc atg agc tct aat     240
Asn Phe Glu Glu Ile Ile Ala Asp Glu Ser Thr Ile Met Ser Ser Asn
65                  70                  75                  80 ttc aac aca gat aga aaa acc cgc ttc att att cat gga ttc ata gac     288
Phe Asn Thr Asp Arg Lys Thr Arg Phe Ile Ile His Gly Phe Ile Asp
                85                  90                  95 aag gga gaa gaa aac tgg ctg tcc aaa ata tgc aag aac ttg ttt aca     336
Lys Gly Glu Glu Asn Trp Leu Ser Lys Ile Cys Lys Asn Leu Phe Thr
            100                 105                 110 gtg gaa agt gtg aac tgc atc tgc gtg gac tgg aaa agt ggc tcc aaa     384
```

-continued

| | | |
|---|---|---|
| Val Glu Ser Val Asn Cys Ile Cys Val Asp Trp Lys Ser Gly Ser Lys<br>115                        120                      125 | | |
| acc ggt tac act cag gcc tca cag aac atc cgg att gtg ggg gca gaa<br>Thr Gly Tyr Thr Gln Ala Ser Gln Asn Ile Arg Ile Val Gly Ala Glu<br>130                        135                      140 | | 432 |
| gtg gca tat ttt gtt gaa gtt ctt cag tca gca ttt ggg tac tca cct<br>Val Ala Tyr Phe Val Glu Val Leu Gln Ser Ala Phe Gly Tyr Ser Pro<br>145                      150                      155                      160 | | 480 |
| tcc aac gtc cac atc att ggc cac agt ctg ggt gcc cac gca gct gga<br>Ser Asn Val His Ile Ile Gly His Ser Leu Gly Ala His Ala Ala Gly<br>                      165                      170                      175 | | 528 |
| gag gca gga agg agg atc aat ggg acg gct ggg cga atc aca ggg ttg<br>Glu Ala Gly Arg Arg Ile Asn Gly Thr Ala Gly Arg Ile Thr Gly Leu<br>                180                      185                      190 | | 576 |
| gat cca gct gaa cct tgc ttt gag ggc aca cct gac tta gtc cga ttg<br>Asp Pro Ala Glu Pro Cys Phe Glu Gly Thr Pro Asp Leu Val Arg Leu<br>                      195                      200                      205 | | 624 |
| gac ccc agc gat gcc ctg ttt gtg gat gta att cac aca gac gct gcc<br>Asp Pro Ser Asp Ala Leu Phe Val Asp Val Ile His Thr Asp Ala Ala<br>210                        215                      220 | | 672 |
| cct ata atc cct aac atg ggg ttt gga atg agc caa acc gta ggc cat<br>Pro Ile Ile Pro Asn Met Gly Phe Gly Met Ser Gln Thr Val Gly His<br>225                      230                      235                      240 | | 720 |
| cta gat ttc ttt cca aat gga gga aaa gaa atg ccc gga tgt cag aag<br>Leu Asp Phe Phe Pro Asn Gly Gly Lys Glu Met Pro Gly Cys Gln Lys<br>                              245                      250                      255 | | 768 |
| aac att ctc tct cag atc gtt gac ata gat ggg atc tgg gaa ggg acc<br>Asn Ile Leu Ser Gln Ile Val Asp Ile Asp Gly Ile Trp Glu Gly Thr<br>                    260                      265                      270 | | 816 |
| cgt gac ttt gtg gcc tgt aat cac tta aga agc tac aag tat tac tct<br>Arg Asp Phe Val Ala Cys Asn His Leu Arg Ser Tyr Lys Tyr Tyr Ser<br>                        275                      280                      285 | | 864 |
| gat agc atc ctt aac ccc gat ggc ttt gca gga ttc cct tgt gcc tct<br>Asp Ser Ile Leu Asn Pro Asp Gly Phe Ala Gly Phe Pro Cys Ala Ser<br>290                        295                      300 | | 912 |
| tac agt gtt ttc tct gca aac aag tgc ttc ccc tgc ccc agt gaa ggc<br>Tyr Ser Val Phe Ser Ala Asn Lys Cys Phe Pro Cys Pro Ser Glu Gly<br>305                        310                      315                      320 | | 960 |
| tgc cca cag atg ggt cat tat gct gac aga ttt cct gga aaa aca aac<br>Cys Pro Gln Met Gly His Tyr Ala Asp Arg Phe Pro Gly Lys Thr Asn<br>                              325                      330                      335 | | 1008 |
| gga gtg ggc cag ata ttt tat cta aac act ggt gat gcc acc aac ttt<br>Gly Val Gly Gln Ile Phe Tyr Leu Asn Thr Gly Asp Ala Thr Asn Phe<br>                    340                      345                      350 | | 1056 |
| gcc cgt tgg agg tat aag gta gct gtc acg ctg tct gga agg aag gtt<br>Ala Arg Trp Arg Tyr Lys Val Ala Val Thr Leu Ser Gly Arg Lys Val<br>                355                      360                      365 | | 1104 |
| aca gga cac gtg cta gtg acc ttg ttt gga aat aaa ggg aat tct aaa<br>Thr Gly His Val Leu Val Thr Leu Phe Gly Asn Lys Gly Asn Ser Lys<br>              370                      375                      380 | | 1152 |
| caa tat gaa att ttc aag ggc act ctc caa ccc gac agc act cac tcc<br>Gln Tyr Glu Ile Phe Lys Gly Thr Leu Gln Pro Asp Ser Thr His Ser<br>385                        390                      395                      400 | | 1200 |
| aac gaa ttt gac tct gat gtg gat gtt gga gat ttg cag aag gtt aaa<br>Asn Glu Phe Asp Ser Asp Val Asp Val Gly Asp Leu Gln Lys Val Lys<br>                              405                      410                      415 | | 1248 |
| ttt att tgg tac aac cgg gtg atc aac cca act cta ccc aga gtg gga<br>Phe Ile Trp Tyr Asn Arg Val Ile Asn Pro Thr Leu Pro Arg Val Gly<br>                    420                      425                      430 | | 1296 |

```
gcg tcc aag atc atg gtg gaa aga aac gac gga aaa gtg ttc aat ttc    1344
Ala Ser Lys Ile Met Val Glu Arg Asn Asp Gly Lys Val Phe Asn Phe
    435                 440                 445 tgt agt caa gaa act gtg agg gaa gat att ctg ctc act ctt acc ccg    1392
Cys Ser Gln Glu Thr Val Arg Glu Asp Ile Leu Leu Thr Leu Thr Pro
450                 455                 460 tgt tag                                                            1398
Cys
465

<210> SEQ ID NO 3
<211> LENGTH: 465
<212> TYPE: PRT
<213> ORGANISM: Felis sp.

<400> SEQUENCE: 3

Met Leu Leu Ile Trp Thr Leu Ser Leu Leu Leu Gly Ala Val Val Gly
1               5                   10                  15

Lys Glu Ile Cys Phe Pro Arg Leu Gly Cys Phe Ser Asp Asp Ala Pro
            20                  25                  30

Trp Ala Gly Ile Ala Gln Arg Pro Leu Lys Ile Leu Pro Trp Pro Pro
        35                  40                  45

Lys Asp Val Asn Thr Arg Phe Leu Leu Tyr Thr Asn Glu Asn Pro Asn
    50                  55                  60

Asn Phe Glu Glu Ile Ile Ala Asp Glu Ser Thr Ile Met Ser Ser Asn
65                  70                  75                  80

Phe Asn Thr Asp Arg Lys Thr Arg Phe Ile Ile His Gly Phe Ile Asp
                85                  90                  95

Lys Gly Glu Glu Asn Trp Leu Ser Lys Ile Cys Lys Asn Leu Phe Thr
            100                 105                 110

Val Glu Ser Val Asn Cys Ile Cys Val Asp Trp Lys Ser Gly Ser Lys
        115                 120                 125

Thr Gly Tyr Thr Gln Ala Ser Gln Asn Ile Arg Ile Val Gly Ala Glu
    130                 135                 140

Val Ala Tyr Phe Val Glu Val Leu Gln Ser Ala Phe Gly Tyr Ser Pro
145                 150                 155                 160

Ser Asn Val His Ile Ile Gly His Ser Leu Gly Ala His Ala Ala Gly
                165                 170                 175

Glu Ala Gly Arg Arg Ile Asn Gly Thr Ala Gly Arg Ile Thr Gly Leu
            180                 185                 190

Asp Pro Ala Glu Pro Cys Phe Glu Gly Thr Pro Asp Leu Val Arg Leu
        195                 200                 205

Asp Pro Ser Asp Ala Leu Phe Val Asp Val Ile His Thr Asp Ala Ala
    210                 215                 220

Pro Ile Ile Pro Asn Met Gly Phe Gly Met Ser Gln Thr Val Gly His
225                 230                 235                 240

Leu Asp Phe Phe Pro Asn Gly Gly Lys Glu Met Pro Gly Cys Gln Lys
                245                 250                 255

Asn Ile Leu Ser Gln Ile Val Asp Ile Asp Gly Ile Trp Glu Gly Thr
            260                 265                 270

Arg Asp Phe Val Ala Cys Asn His Leu Arg Ser Tyr Lys Tyr Tyr Ser
        275                 280                 285

Asp Ser Ile Leu Asn Pro Asp Gly Phe Ala Gly Phe Pro Cys Ala Ser
    290                 295                 300

Tyr Ser Val Phe Ser Ala Asn Lys Cys Phe Pro Cys Pro Ser Glu Gly
305                 310                 315                 320
```

```
Cys Pro Gln Met Gly His Tyr Ala Asp Arg Phe Pro Gly Lys Thr Asn
              325                 330                 335
Gly Val Gly Gln Ile Phe Tyr Leu Asn Thr Gly Asp Ala Thr Asn Phe
              340                 345                 350
Ala Arg Trp Arg Tyr Lys Val Ala Val Thr Leu Ser Gly Arg Lys Val
              355                 360                 365
Thr Gly His Val Leu Val Thr Leu Phe Gly Asn Lys Gly Asn Ser Lys
              370                 375                 380
Gln Tyr Glu Ile Phe Lys Gly Thr Leu Gln Pro Asp Ser Thr His Ser
385                 390                 395                 400
Asn Glu Phe Asp Ser Asp Val Asp Val Gly Asp Leu Gln Lys Val Lys
              405                 410                 415
Phe Ile Trp Tyr Asn Arg Val Ile Asn Pro Thr Leu Pro Arg Val Gly
              420                 425                 430
Ala Ser Lys Ile Met Val Glu Arg Asn Asp Gly Lys Val Phe Asn Phe
              435                 440                 445
Cys Ser Gln Glu Thr Val Arg Glu Asp Ile Leu Leu Thr Leu Thr Pro
    450                 455                 460
Cys
465

<210> SEQ ID NO 4
<211> LENGTH: 30
<212> TYPE: DNA
<213> ORGANISM: Artificial
<220> FEATURE:
<223> OTHER INFORMATION: Artificial Sequence, RACE5 primer
<220> FEATURE:
<221> NAME/KEY: misc_feature
<222> LOCATION: (19)..(19)
<223> OTHER INFORMATION: h is a, c, or t
<220> FEATURE:
<221> NAME/KEY: misc_feature
<222> LOCATION: (20)..(20)
<223> OTHER INFORMATION: r is a or g
<220> FEATURE:
<221> NAME/KEY: misc_feature
<222> LOCATION: (25)..(25)
<223> OTHER INFORMATION: y is c or t
<220> FEATURE:
<221> NAME/KEY: misc_feature
<222> LOCATION: (28)..(28)
<223> OTHER INFORMATION: s is c or g
<220> FEATURE:
<221> NAME/KEY: misc_feature
<222> LOCATION: (29)..(29)
<223> OTHER INFORMATION: r is a or g

<400> SEQUENCE: 4
gatcctgccc tggagcccchr aggaygtsra                                     30

<210> SEQ ID NO 5
<211> LENGTH: 45
<212> TYPE: DNA
<213> ORGANISM: Artificial
<220> FEATURE:
<223> OTHER INFORMATION: Artificial Sequence, UPM primer

<400> SEQUENCE: 5
ctaatacgac tcactatagg gcaagcagtg gtatcaacgc agagt                     45

<210> SEQ ID NO 6
<211> LENGTH: 22
<212> TYPE: DNA
```

```
<213> ORGANISM: Artificial
<220> FEATURE:
<223> OTHER INFORMATION: Artificial sequence, UPM primer

<400> SEQUENCE: 6
ctaatacgac tcactatagg gc                                            22

<210> SEQ ID NO 7
<211> LENGTH: 23
<212> TYPE: DNA
<213> ORGANISM: Artificial
<220> FEATURE:
<223> OTHER INFORMATION: Artificial sequence, Kc616 primer

<400> SEQUENCE: 7 caccottctg cccccacaat ccg                                           23

<210> SEQ ID NO 8
<211> LENGTH: 36
<212> TYPE: DNA
<213> ORGANISM: Artificial
<220> FEATURE:
<223> OTHER INFORMATION: Artificial sequence, Kc626 primer

<400> SEQUENCE: 8
aagaattcag ccaccatgct gctaatctgg acacta                             36

<210> SEQ ID NO 9
<211> LENGTH: 35
<212> TYPE: DNA
<213> ORGANISM: Artificial
<220> FEATURE:
<223> OTHER INFORMATION: Artificial sequence, Kc630 primer

<400> SEQUENCE: 9
tcgcggccgc tcaacacgga gtaagagtga gcaga                              35

<210> SEQ ID NO 10
<211> LENGTH: 32
<212> TYPE: DNA
<213> ORGANISM: Artificial
<220> FEATURE:
<223> OTHER INFORMATION: Artificial sequence, fpl-4_xho1Stop primer

<400> SEQUENCE: 10
gctcgagcta ctatgcacac ggggtaagag tg                                 32

<210> SEQ ID NO 11
<211> LENGTH: 33
<212> TYPE: DNA
<213> ORGANISM: Artificial
<220> FEATURE:
<223> OTHER INFORMATION: Artificial sequence, fpl-3_HindIII primer

<400> SEQUENCE: 11
caagcttacc atggtgctaa tctggacact atc                                33

<210> SEQ ID NO 12
<211> LENGTH: 465
<212> TYPE: PRT
<213> ORGANISM: Rattus norvegicus

<400> SEQUENCE: 12

Met Leu Met Leu Trp Thr Phe Ala Val Leu Leu Gly Ala Val Ala Gly
1               5                   10                  15
```

```
Lys Glu Val Cys Phe Asp Lys Leu Gly Cys Phe Ser Asp Asp Ala Pro
             20                  25                  30

Trp Ser Gly Thr Ile Asp Arg Pro Leu Lys Ala Leu Pro Trp Ser Pro
         35                  40                  45

Ala Gln Ile Asn Thr Arg Phe Leu Leu Tyr Thr Asn Glu Asn Gln Asp
     50                  55                  60

Asn Tyr Gln Lys Ile Thr Ser Asp Ala Ser Ser Ile Arg Asn Ser Asn
 65                  70                  75                  80

Phe Lys Thr Asn Arg Lys Thr Arg Ile Ile His Gly Phe Ile Asp
                 85                  90                  95

Lys Gly Glu Glu Asn Trp Leu Ser Asp Met Cys Lys Asn Met Phe Lys
             100                 105                 110

Val Glu Ser Val Asn Cys Ile Cys Val Asp Trp Lys Gly Ser Arg
             115                 120                 125

Ala Thr Tyr Thr Gln Ala Thr Gln Asn Val Arg Val Gly Ala Glu
         130                 135                 140

Val Ala Leu Leu Val Asn Val Leu Lys Ser Asp Leu Gly His Pro Pro
145                 150                 155                 160

Asp Asn Val His Leu Ile Gly His Ser Leu Gly Ser His Val Ala Gly
                 165                 170                 175

Glu Ala Gly Lys Arg Thr Phe Gly Ala Ile Gly Arg Ile Thr Gly Leu
             180                 185                 190

Asp Ala Ala Glu Pro Tyr Phe Gln Gly Thr Pro Glu Glu Val Arg Leu
         195                 200                 205

Asp Pro Thr Asp Ala Gln Phe Val Asp Ala Ile His Thr Asp Ala Ala
     210                 215                 220

Pro Ile Ile Pro Asn Leu Gly Phe Gly Met Ser Gln Thr Val Gly His
225                 230                 235                 240

Leu Asp Phe Phe Pro Asn Gly Gly Met Glu Met Pro Gly Cys Gln Lys
                 245                 250                 255

Asn Ile Leu Ser Gln Ile Val Asp Ile Asp Gly Ile Trp Glu Gly Thr
             260                 265                 270

Arg Asp Phe Ala Ala Cys Asn His Leu Arg Ser Tyr Lys Tyr Tyr Thr
         275                 280                 285

Asp Ser Ile Val Asn Pro Thr Gly Phe Ser Gly Phe Ser Cys Ser Ser
     290                 295                 300

Tyr Asn Val Phe Ser Ala Asn Lys Cys Phe Pro Cys Gly Ser Glu Gly
305                 310                 315                 320

Cys Pro Gln Met Gly His Tyr Ala Asp Lys Tyr Pro Gly Lys Thr Lys
                 325                 330                 335

Glu Leu Tyr Gln Lys Phe Tyr Leu Asn Thr Gly Asp Lys Ser Asn Phe
             340                 345                 350

Ala Arg Trp Arg Tyr Gln Val Thr Val Thr Leu Ser Gly Gln Lys Val
         355                 360                 365

Thr Gly His Ile Leu Val Ser Leu Phe Gly Asn Gly Asn Ser Lys
     370                 375                 380

Gln Tyr Glu Val Phe Lys Gly Ser Leu His Pro Gly Asp Thr His Val
385                 390                 395                 400

Lys Glu Phe Asp Ser Asp Met Asp Val Gly Asp Leu Gln Lys Val Lys
                 405                 410                 415

Phe Ile Trp Tyr Asn Asn Val Ile Asn Pro Thr Leu Pro Lys Val Gly
             420                 425                 430

Ala Ser Arg Ile Ser Val Glu Arg Asn Asp Gly Arg Val Phe Asn Phe
```

```
                435                 440                 445
Cys Ser Gln Asp Thr Val Arg Glu Asp Val Leu Leu Thr Leu Ser Ala
    450                 455                 460
Cys
465

<210> SEQ ID NO 13
<211> LENGTH: 465
<212> TYPE: PRT
<213> ORGANISM: Mus musculus

<400> SEQUENCE: 13

Met Leu Met Leu Trp Thr Phe Ala Val Leu Leu Gly Ala Val Ala Gly
1               5                   10                  15

Arg Glu Val Cys Phe Asp Lys Leu Gly Cys Phe Ser Asp Asp Ala Pro
            20                  25                  30

Trp Ser Gly Thr Leu Asp Arg Pro Leu Lys Ala Leu Pro Trp Ser Pro
        35                  40                  45

Ala Gln Ile Asn Thr Arg Phe Leu Leu Tyr Thr Asn Glu Asn Pro Asp
    50                  55                  60

Asn Tyr Gln Leu Ile Thr Ser Asp Ala Ser Asn Ile Arg Asn Ser Asn
65                  70                  75                  80

Phe Arg Thr Asn Arg Lys Thr Arg Ile Ile His Gly Phe Ile Asp
                85                  90                  95

Lys Gly Glu Glu Asn Trp Leu Ser Asp Met Cys Lys Asn Met Phe Arg
            100                 105                 110

Val Glu Ser Val Asn Cys Ile Cys Val Asp Trp Lys Gly Gly Ser Arg
        115                 120                 125

Thr Thr Tyr Thr Gln Ala Thr Gln Asn Val Arg Val Val Gly Ala Glu
    130                 135                 140

Val Ala Leu Leu Val Asn Val Leu Gln Ser Asp Leu Gly Tyr Ser Leu
145                 150                 155                 160

Asn Asn Val His Leu Ile Gly His Ser Leu Gly Ser His Ile Ala Gly
                165                 170                 175

Glu Ala Gly Lys Arg Thr Phe Gly Ala Ile Gly Arg Ile Thr Gly Leu
            180                 185                 190

Asp Pro Ala Glu Pro Tyr Phe Gln Gly Thr Pro Glu Glu Val Arg Leu
        195                 200                 205

Asp Pro Thr Asp Ala Gln Phe Val Asp Ala Ile His Thr Asp Ala Gly
    210                 215                 220

Pro Ile Ile Pro Asn Leu Gly Phe Gly Met Ser Gln Thr Val Gly His
225                 230                 235                 240

Leu Asp Phe Phe Pro Asn Gly Gly Ile Glu Met Pro Gly Cys Gln Lys
                245                 250                 255

Asn Ile Leu Ser Gln Ile Val Asp Ile Asp Gly Ile Trp Glu Gly Thr
            260                 265                 270

Arg Asn Phe Ala Ala Cys Asn His Leu Arg Ser Tyr Lys Phe Tyr Thr
        275                 280                 285

Asp Ser Ile Val Asn Pro Thr Gly Phe Ala Gly Phe Ser Cys Ser Ser
    290                 295                 300

Tyr Ser Leu Phe Thr Ala Asn Lys Cys Phe Pro Cys Gly Ser Gly Gly
305                 310                 315                 320

Cys Pro Gln Met Gly His Tyr Ala Asp Arg Tyr Pro Gly Lys Thr Ser
                325                 330                 335
```

-continued

```
Arg Leu Tyr Gln Thr Phe Tyr Leu Asn Thr Gly Asp Lys Ser Asn Phe
                340                 345                 350

Ala Arg Trp Arg Tyr Gln Val Thr Val Thr Leu Ser Gly Gln Lys Val
            355                 360                 365

Thr Gly His Ile Leu Val Ser Leu Phe Gly Asn Gly Gly Asn Ser Lys
        370                 375                 380

Gln Tyr Glu Val Phe Lys Gly Ser Leu Gln Pro Gly Thr Ser His Val
385                 390                 395                 400

Asn Glu Phe Asp Ser Asp Val Asp Val Gly Asp Leu Gln Lys Val Lys
                405                 410                 415

Phe Ile Trp Tyr Asn Asn Val Ile Asn Pro Thr Leu Pro Lys Val Gly
            420                 425                 430

Ala Ser Arg Ile Thr Val Glu Arg Asn Asp Gly Arg Val Phe Asn Phe
        435                 440                 445

Cys Ser Gln Glu Thr Val Arg Glu Asp Val Leu Leu Thr Leu Ser Pro
    450                 455                 460

Cys
465

<210> SEQ ID NO 14
<211> LENGTH: 465
<212> TYPE: PRT
<213> ORGANISM: Homo sapiens

<400> SEQUENCE: 14

Met Leu Pro Leu Trp Thr Leu Ser Leu Leu Gly Ala Val Ala Gly
1               5                   10                  15

Lys Glu Val Cys Tyr Glu Arg Leu Gly Cys Phe Ser Asp Asp Ser Pro
                20                  25                  30

Trp Ser Gly Ile Thr Glu Arg Pro Leu His Ile Leu Pro Trp Ser Pro
            35                  40                  45

Lys Asp Val Asn Thr Arg Phe Leu Leu Tyr Thr Asn Glu Asn Pro Asn
        50                  55                  60

Asn Phe Gln Glu Val Ala Ala Asp Ser Ser Ile Ser Gly Ser Asn
65                  70                  75                  80

Phe Lys Thr Asn Arg Lys Thr Arg Phe Ile Ile His Gly Phe Ile Asp
                85                  90                  95

Lys Gly Glu Glu Asn Trp Leu Ala Asn Val Cys Lys Asn Leu Phe Lys
            100                 105                 110

Val Glu Ser Val Asn Cys Ile Cys Val Asp Trp Lys Gly Gly Ser Arg
        115                 120                 125

Thr Gly Tyr Thr Gln Ala Ser Gln Asn Ile Arg Ile Val Gly Ala Glu
    130                 135                 140

Val Ala Tyr Phe Val Glu Phe Leu Gln Ser Ala Phe Gly Tyr Ser Pro
145                 150                 155                 160

Ser Asn Val His Val Ile Gly His Ser Leu Gly Ala His Ala Ala Gly
                165                 170                 175

Glu Ala Gly Arg Arg Thr Asn Gly Thr Ile Gly Arg Ile Thr Gly Leu
            180                 185                 190

Asp Pro Ala Glu Pro Cys Phe Gln Gly Thr Pro Glu Leu Val Arg Leu
        195                 200                 205

Asp Pro Ser Asp Ala Lys Phe Val Asp Val Ile His Thr Asp Gly Ala
    210                 215                 220

Pro Ile Val Pro Asn Leu Gly Phe Gly Met Ser Gln Val Gly His
225                 230                 235                 240
```

```
Leu Asp Phe Phe Pro Asn Gly Gly Val Glu Met Pro Gly Cys Lys Lys
                245                 250                 255

Asn Ile Leu Ser Gln Ile Val Asp Ile Asp Gly Ile Trp Glu Gly Thr
            260                 265                 270

Arg Asp Phe Ala Ala Cys Asn His Leu Arg Ser Tyr Lys Tyr Tyr Thr
        275                 280                 285

Asp Ser Ile Val Asn Pro Asp Gly Phe Ala Gly Phe Pro Cys Ala Ser
    290                 295                 300

Tyr Asn Val Phe Thr Ala Asn Lys Cys Phe Pro Cys Pro Ser Gly Gly
305                 310                 315                 320

Cys Pro Gln Met Gly His Tyr Ala Asp Arg Tyr Pro Gly Lys Thr Asn
                325                 330                 335

Asp Val Gly Gln Lys Phe Tyr Leu Asp Thr Gly Asp Ala Ser Asn Phe
            340                 345                 350

Ala Arg Trp Arg Tyr Lys Val Ser Val Thr Leu Ser Gly Lys Lys Val
        355                 360                 365

Thr Gly His Ile Leu Val Ser Leu Phe Gly Asn Lys Gly Asn Ser Lys
    370                 375                 380

Gln Tyr Glu Ile Phe Lys Gly Thr Leu Lys Pro Asp Ser Thr His Ser
385                 390                 395                 400

Asn Glu Phe Asp Ser Asp Val Asp Val Gly Asp Leu Gln Met Val Lys
                405                 410                 415

Phe Ile Trp Tyr Asn Asn Val Ile Asn Pro Thr Leu Pro Arg Val Gly
            420                 425                 430

Ala Ser Lys Ile Ile Val Glu Thr Asn Val Gly Lys Gln Phe Asn Phe
        435                 440                 445

Cys Ser Pro Glu Thr Val Arg Glu Glu Val Leu Thr Leu Thr Pro
    450                 455                 460

Cys
465

<210> SEQ ID NO 15
<211> LENGTH: 461
<212> TYPE: PRT
<213> ORGANISM: Equus caballus

<400> SEQUENCE: 15

Trp Thr Leu Ser Leu Leu Gly Ala Val Val Gly Asn Glu Val Cys
1               5                   10                  15

Tyr Glu Arg Leu Gly Cys Phe Ser Asp Asp Ser Pro Trp Ala Gly Ile
            20                  25                  30

Val Glu Arg Pro Leu Lys Ile Leu Pro Trp Ser Pro Glu Lys Val Asn
        35                  40                  45

Thr Arg Phe Leu Leu Tyr Thr Asn Glu Asn Pro Asp Asn Phe Gln Glu
    50                  55                  60

Ile Val Ala Asp Pro Ser Thr Ile Gln Ser Ser Asn Phe Asn Thr Gly
65                  70                  75                  80

Arg Lys Thr Arg Phe Ile Ile His Gly Phe Ile Asp Lys Gly Glu Glu
                85                  90                  95

Ser Trp Leu Ser Thr Met Cys Gln Asn Met Phe Lys Val Glu Ser Val
            100                 105                 110

Asn Cys Ile Cys Val Asp Trp Lys Ser Gly Ser Arg Thr Ala Tyr Ser
        115                 120                 125

Gln Ala Ser Gln Asn Val Arg Ile Val Gly Ala Glu Val Ala Tyr Leu
```

130                 135                 140
Val Gly Val Leu Gln Ser Ser Phe Asp Tyr Ser Pro Ser Asn Val His
145                 150                 155                 160

Ile Ile Gly His Ser Leu Gly Ser His Ala Ala Gly Glu Ala Gly Arg
                165                 170                 175

Arg Thr Asn Gly Ala Val Gly Arg Ile Thr Gly Leu Asp Pro Ala Glu
                180                 185                 190

Pro Cys Phe Gln Gly Thr Pro Glu Leu Val Arg Leu Asp Pro Ser Asp
                195                 200                 205

Ala Gln Phe Val Asp Val Ile His Thr Asp Ile Ala Pro Phe Ile Pro
210                 215                 220

Asn Leu Gly Phe Gly Met Ser Gln Thr Ala Gly His Leu Asp Phe Phe
225                 230                 235                 240

Pro Asn Gly Gly Lys Glu Met Pro Gly Cys Gln Lys Asn Val Leu Ser
                245                 250                 255

Gln Ile Val Asp Ile Asp Gly Ile Trp Gln Gly Thr Arg Asp Phe Ala
                260                 265                 270

Ala Cys Asn His Leu Arg Ser Tyr Lys Tyr Tyr Thr Asp Ser Ile Leu
                275                 280                 285

Asn Pro Asp Gly Phe Ala Gly Phe Ser Cys Ala Ser Tyr Ser Asp Phe
                290                 295                 300

Thr Ala Asn Lys Cys Phe Pro Cys Ser Ser Glu Gly Cys Pro Gln Met
305                 310                 315                 320

Gly His Tyr Ala Asp Arg Phe Pro Gly Arg Thr Lys Gly Val Gly Gln
                325                 330                 335

Leu Phe Tyr Leu Asn Thr Gly Asp Ala Ser Asn Phe Ala Arg Trp Arg
                340                 345                 350

Tyr Arg Val Asp Val Thr Leu Ser Gly Lys Lys Val Thr Gly His Val
                355                 360                 365

Leu Val Ser Leu Phe Gly Asn Lys Gly Asn Ser Arg Gln Tyr Glu Ile
                370                 375                 380

Phe Gln Gly Thr Leu Lys Pro Asp Asn Thr Tyr Ser Asn Glu Phe Asp
385                 390                 395                 400

Ser Asp Val Glu Val Gly Asp Leu Glu Lys Val Lys Phe Ile Trp Tyr
                405                 410                 415

Asn Asn Val Ile Asn Leu Thr Leu Pro Lys Val Gly Ala Ser Lys Ile
                420                 425                 430

Thr Val Glu Arg Asn Asp Gly Ser Val Phe Asn Phe Cys Ser Glu Glu
                435                 440                 445

Thr Val Arg Glu Asp Val Leu Leu Thr Leu Thr Ala Cys
450                 455                 460

<210> SEQ ID NO 16
<211> LENGTH: 467
<212> TYPE: PRT
<213> ORGANISM: Canis familiaris

<400> SEQUENCE: 16

Met Val Ser Ile Trp Thr Ile Ala Leu Phe Leu Leu Gly Ala Ala Lys
1               5                   10                  15

Ala Lys Glu Val Cys Tyr Glu Gln Ile Gly Cys Phe Ser Asp Ala Glu
                20                  25                  30

Pro Trp Ala Gly Thr Ala Ile Arg Pro Leu Lys Val Leu Pro Trp Ser
                35                  40                  45

```
Pro Glu Arg Ile Gly Thr Arg Phe Leu Leu Tyr Thr Asn Lys Asn Pro
 50                  55                  60

Asn Asn Phe Gln Thr Leu Leu Pro Ser Asp Pro Ser Thr Ile Glu Ala
 65                  70                  75                  80

Ser Asn Phe Gln Thr Asp Lys Lys Thr Arg Phe Thr Ile His Gly Phe
                 85                  90                  95

Ile Asn Lys Gly Glu Glu Asn Trp Leu Leu Asp Met Cys Lys Asn Met
            100                 105                 110

Phe Lys Val Glu Glu Val Asn Cys Ile Cys Val Asp Trp Lys Lys Gly
        115                 120                 125

Ser Gln Thr Ser Tyr Thr Gln Ala Ala Asn Asn Val Arg Val Val Gly
    130                 135                 140

Ala Gln Val Ala Gln Met Leu Ser Met Leu Ser Ala Asn Tyr Ser Tyr
145                 150                 155                 160

Ser Pro Ser Gln Val Gln Leu Ile Gly His Ser Leu Gly Ala His Val
                165                 170                 175

Ala Gly Glu Ala Gly Ser Arg Thr Pro Gly Leu Gly Arg Ile Thr Gly
            180                 185                 190

Leu Asp Pro Val Glu Ala Ser Phe Gln Gly Thr Pro Glu Glu Val Arg
        195                 200                 205

Leu Asp Pro Thr Asp Ala Asp Phe Val Asp Val Ile His Thr Asp Ala
    210                 215                 220

Ala Pro Leu Ile Pro Phe Leu Gly Phe Gly Thr Ser Gln Gln Met Gly
225                 230                 235                 240

His Leu Asp Phe Phe Pro Asn Gly Gly Glu Glu Met Pro Gly Cys Lys
                245                 250                 255

Lys Asn Ala Leu Ser Gln Ile Val Asn Leu Asp Gly Ile Trp Glu Gly
            260                 265                 270

Thr Arg Asp Phe Val Ala Cys Asn His Leu Arg Ser Tyr Lys Tyr Tyr
        275                 280                 285

Ser Glu Ser Ile Leu Asn Pro Asp Gly Phe Ala Ser Tyr Pro Cys Ala
    290                 295                 300

Ser Tyr Arg Ala Phe Glu Ser Asn Lys Cys Phe Pro Cys Pro Asp Gln
305                 310                 315                 320

Gly Cys Pro Gln Met Gly His Tyr Ala Asp Lys Phe Ala Val Lys Thr
                325                 330                 335

Ser Asp Glu Thr Gln Lys Tyr Phe Leu Asn Thr Gly Asp Ser Ser Asn
            340                 345                 350

Phe Ala Arg Trp Arg Tyr Gly Val Ser Ile Thr Leu Ser Gly Lys Arg
        355                 360                 365

Ala Thr Gly Gln Ala Lys Val Ala Leu Phe Gly Ser Lys Gly Asn Thr
    370                 375                 380

His Gln Phe Asn Ile Phe Lys Gly Ile Leu Lys Pro Gly Ser Thr His
385                 390                 395                 400

Ser Asn Glu Phe Asp Ala Lys Leu Asp Val Gly Thr Ile Glu Lys Val
                405                 410                 415

Lys Phe Leu Trp Asn Asn Asn Val Val Asn Pro Thr Phe Pro Lys Val
            420                 425                 430

Gly Ala Ala Lys Ile Thr Val Gln Lys Gly Glu Glu Lys Thr Val His
        435                 440                 445
```

```
Ser Phe Cys Ser Glu Ser Thr Val Arg Glu Asp Val Leu Leu Thr Leu
    450                 455             460

Thr Pro Cys
465
```